(12) United States Patent
Furuta et al.

(10) Patent No.: US 11,026,763 B2
(45) Date of Patent: Jun. 8, 2021

(54) PROJECTION MAPPING APPARATUS

(71) Applicant: FUJIFILM Corporation, Tokyo (JP)

(72) Inventors: Yoshinori Furuta, Saitama (JP);
Tomoyuki Kawai, Saitama (JP);
Tomonori Masuda, Saitama (JP);
Junya Kitagawa, Saitama (JP);
Yasuhiro Shinkai, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 570 days.

(21) Appl. No.: 15/928,651

(22) Filed: Mar. 22, 2018

(65) Prior Publication Data

US 2018/0214241 A1 Aug. 2, 2018

Related U.S. Application Data

(63) Continuation of application No. PCT/JP2016/074250, filed on Aug. 19, 2016.

(30) Foreign Application Priority Data

Sep. 28, 2015 (JP) .............................. JP2015-189531

(51) Int. Cl.
*A61B 90/00* (2016.01)
*A61B 34/20* (2016.01)
(Continued)

(52) U.S. Cl.
CPC ............ *A61B 90/361* (2016.02); *A61B 34/20* (2016.02); *A61B 90/36* (2016.02);
(Continued)

(58) Field of Classification Search
CPC ....... A61B 90/361; A61B 90/36; A61B 34/20; A61B 2090/309; A61B 2034/105;
(Continued)

(56) References Cited

U.S. PATENT DOCUMENTS 6,275,724 B1 8/2001 Dickinson et al.
9,625,258 B2 * 4/2017 Deichmann ............ H04N 13/25
(Continued)

FOREIGN PATENT DOCUMENTS

CN 102429728 A 5/2012
CN 102920513 A 2/2013
(Continued)

OTHER PUBLICATIONS

Japanese Office Action, dated Jul. 17, 2019, for Japanese Application No. 2018-186738, with an English machine translation.
(Continued)

*Primary Examiner* — Luther Behringer
*Assistant Examiner* — Amy J Shafqat
(74) *Attorney, Agent, or Firm* — Birch, Stewart, Kolasch & Birch, LLP.

(57) ABSTRACT

A received light signal of the measurement light which is reflected from the subject and is then incident on a distance image sensor is acquired from the distance image sensor and a distance image is generated on the basis of the acquired received light signal. The position of a leading end of a medical instrument inserted into the subject is acquired. A leading end position image indicating the position of the leading end of the medical instrument in the subject is acquired. A projection image which is projected to the subject and corresponds to a surface shape of a corresponding part of the subject corresponding to the position of the leading end is generated from the leading end position image, on the basis of the shape of the subject detected from the distance image and the position of the leading end. The projection image is projected to the corresponding part.

11 Claims, 26 Drawing Sheets

(51) Int. Cl.
| | |
|---|---|
| *G01B 11/25* | (2006.01) |
| *A61B 90/30* | (2016.01) |
| *A61B 34/10* | (2016.01) |
| *A61B 17/00* | (2006.01) |
| *A61B 6/00* | (2006.01) |

(52) U.S. Cl.
CPC ........ *G01B 11/2513* (2013.01); *A61B 6/4283* (2013.01); *A61B 2017/00154* (2013.01); *A61B 2034/105* (2016.02); *A61B 2034/2048* (2016.02); *A61B 2034/2055* (2016.02); *A61B 2034/2057* (2016.02); *A61B 2034/2072* (2016.02); *A61B 2090/309* (2016.02); *A61B 2090/366* (2016.02); *A61B 2090/376* (2016.02)

(58) Field of Classification Search
CPC .... A61B 2090/376; A61B 2017/00154; A61B 2034/2048; A61B 2034/2055; A61B 2034/2057; A61B 2034/2072; A61B 2090/366; A61B 6/4283; G01B 11/2513; G01B 11/2518; G01B 11/254; G01B 11/24
See application file for complete search history.

(56) References Cited

U.S. PATENT DOCUMENTS

| | | | | |
|---|---|---|---|---|
| 9,697,639 | B2* | 7/2017 | Masumoto | G06T 7/12 |
| 10,648,789 | B2* | 5/2020 | Klimov | G01B 11/002 |
| 10,716,457 | B2* | 7/2020 | Pheiffer | G06T 17/10 |
| 2002/0077533 | A1 | 6/2002 | Bieger et al. | |
| 2005/0195587 | A1 | 9/2005 | Moctezuma De La Barrera et al. | |
| 2006/0173299 | A1 | 8/2006 | Romley et al. | |
| 2007/0201609 | A1 | 8/2007 | Ohishi et al. | |
| 2008/0094643 | A1* | 4/2008 | Nishio | G01B 11/026 |
| | | | | 356/623 |
| 2012/0071765 | A1* | 3/2012 | Chinnock | A61B 5/0075 |
| | | | | 600/476 |
| 2012/0130258 | A1* | 5/2012 | Taylor | A61B 3/18 |
| | | | | 600/476 |
| 2014/0055771 | A1* | 2/2014 | Oggier | G01S 17/89 |
| | | | | 356/5.01 |
| 2014/0236000 | A1 | 8/2014 | Kozuka et al. | |
| 2015/0177598 | A1 | 6/2015 | Mima et al. | |
| 2015/0181153 | A1* | 6/2015 | Mima | G03B 15/14 |
| | | | | 348/333.1 |
| 2015/0300816 | A1* | 10/2015 | Yang | G01N 21/4738 |
| | | | | 600/424 |
| 2017/0024903 | A1* | 1/2017 | Razzaque | A61B 6/463 |
| 2018/0014901 | A1* | 1/2018 | Saito | A61B 90/00 |

FOREIGN PATENT DOCUMENTS

| | | |
|---|---|---|
| DE | 10008806 A1 | 12/2001 |
| JP | 2002-102251 A | 4/2002 |
| JP | 2002-509748 A | 4/2002 |
| JP | 2003-14430 A | 1/2003 |
| JP | 2007-151686 A | 6/2007 |
| JP | 2007-229473 A | 9/2007 |
| JP | 2008-522789 A | 7/2008 |
| JP | 2011-161091 A | 8/2011 |
| JP | 2013-236757 A | 11/2013 |
| JP | 2014-212904 A | 11/2014 |
| JP | 2015-111772 A | 6/2015 |
| WO | WO 2014/024422 A1 | 2/2014 |
| WO | WO 2015/001806 A1 | 1/2015 |

OTHER PUBLICATIONS

International Preliminary Report on Patentability (form PCT/IPEA/409) dated Mar. 1, 2017, for International Application No. PCT/JP2016/074250, with an English translation.

International Search Report and Written Opinion of the International Searching Authority (forms PCT/ISA/210 and PCT/ISA/237), dated Nov. 22, 2016, for International Application No. PCT/JP2016/074250, with an English translation of the International Search Report.

Chinese Office Action and Search Report for Chinese Application No. 201680054781.X, dated Apr. 14, 2020, with English translation.

* cited by examiner

<PATIENT>

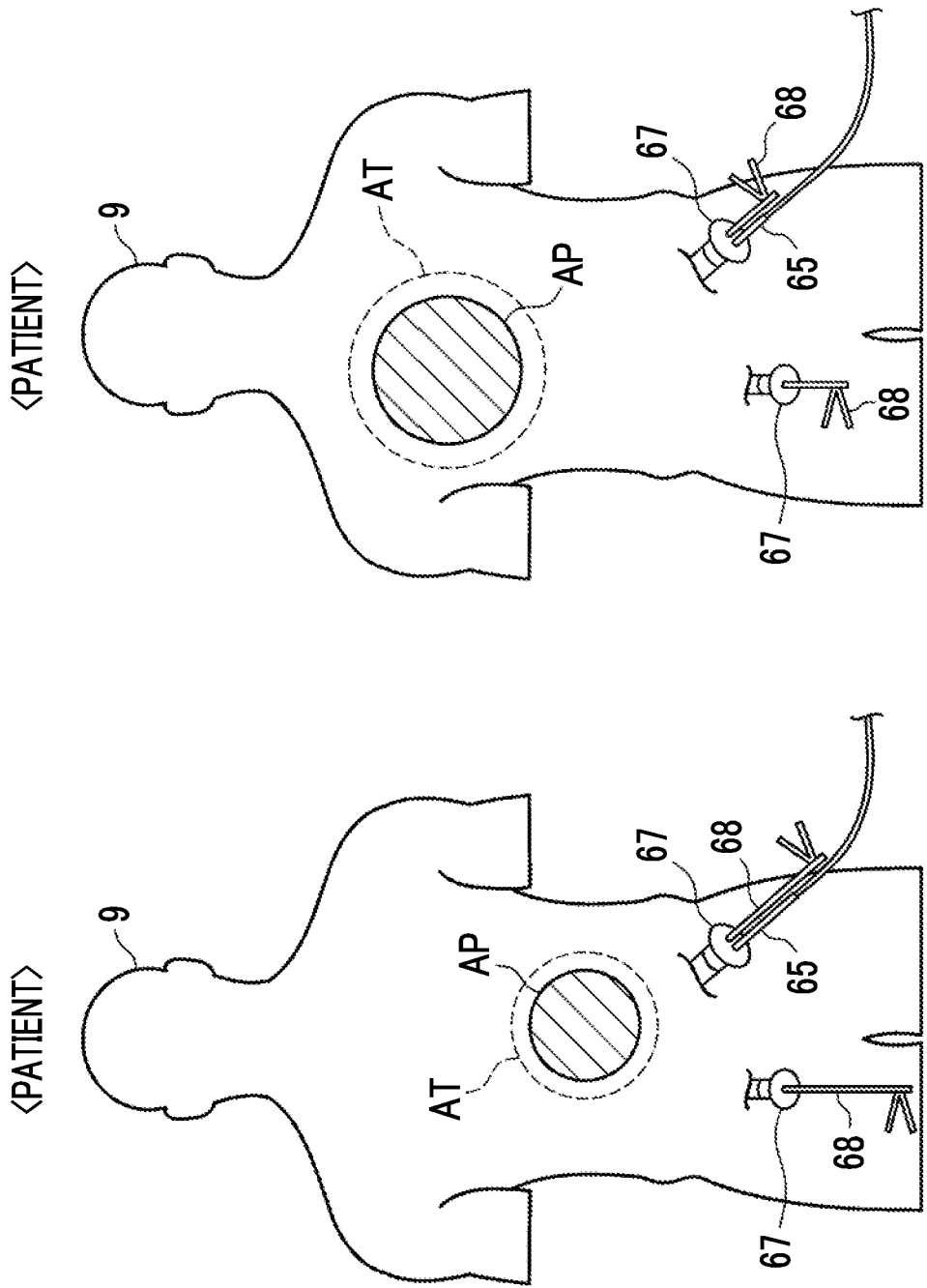

PROJECTION MAPPING APPARATUS

CROSS-REFERENCE TO RELATED APPLICATIONS

The present application is a Continuation of PCT International Application No. PCT/JP2016/074250 filed on Aug. 19, 2016 claiming priority under 35 U.S.C § 119(a) to Japanese Patent Application No. 2015-189531 filed on Sep. 28, 2015. Each of the above applications is hereby expressly incorporated by reference, in their entirety, into the present application.

BACKGROUND OF THE INVENTION

1. Field of the Invention

The present invention relates to a projection mapping apparatus that projects an image to a subject into which a medical instrument is inserted.

2. Description of the Related Art

In a medical field, a technique has been known which projects the image of, for example, the organs, muscle, bones, joints, and blood vessels to a patient using a projector device. JP2007-151686A discloses a projection system which captures an image of a patient having a thermal marker attached thereto using an infrared camera, analyzes a captured infrared image to estimate the position and posture of the patient (subject), and projects information (for example, the organs) about the inside of the body of the patient according to the position and posture of the patient on the basis of the estimation result.

JP2002-102251A discloses an apparatus which detects the space coordinates of a medical instrument (surgical instrument) inserted into the body of a patient and projects a geometric pattern related to, for example, the position and orientation of the medical instrument to the patient on the basis of the detection result of the space coordinates. In the apparatus disclosed in JP2002-102251A, the position of the geometric pattern projected to the patient indicates the position (two-dimensional position) of the medical instrument in the body of the patient and the color of the geometric pattern indicates the depth position of the medical instrument in the body of the patient.

SUMMARY OF THE INVENTION

However, the technique disclosed in JP2007-151686A can estimate the position or posture of the patient, but is not capable of determining the shape of a projection surface (irradiation surface) of the patient to which the information (for example, the organs) about the inside of the body is projected. Therefore, there is a concern that the projection image (irradiation image) projected to the projection surface of the patient will be distorted. As a result, it is difficult to reproduce the shape or size of the information (for example, the organs) about the inside of the body on the projection image projected to the patient.

In the technique disclosed in JP2002-102251A, the geometric pattern is projected as the projection image to the patient. However, it is assumed that the position of the patient is not moved and it is difficult to determine the shape of the projection surface (irradiation surface) of the patient to which the geometric pattern is projected. Therefore, in the technique disclosed in JP2002-102251A, in a case in which the patient moves, there is a concern that the position of the projection image in the geometric pattern will be shifted or the projection image will be distorted as in JP2007-151686A. As a result, in some cases, it is difficult to reproduce at least the position of the medical instrument inserted into the body of the patient in the projection image disclosed in JP2002-102251A.

The invention has been made in view of the above-mentioned problems and relates to a projection mapping apparatus that can project a projection image indicating the position of a leading end of a medical instrument inserted into a subject in response to a change in the position or posture of the subject.

In order to achieve the object of the invention, there is provided a projection mapping apparatus including: a light source that irradiates a subject with measurement light; a distance image sensor in which a plurality of light receiving elements are two-dimensionally arranged; a distance image generation unit that acquires a received light signal of the measurement light which is emitted from the light source, is reflected from the subject, and is incident on the distance image sensor from the distance image sensor and generates a distance image on the basis of the acquired received light signal; a position information acquisition unit that acquires a position of a leading end of a medical instrument inserted into the subject; a leading end position image acquisition unit that acquires a leading end position image indicating the position of the leading end of the medical instrument in the subject; a projection image generation unit that generates a projection image corresponding to a surface shape of a corresponding part of the subject which corresponds to the position of the leading end from the leading end position image acquired by the leading end position image acquisition unit, on the basis of a shape of the subject detected from the distance image generated by the distance image generation unit and the position of the leading end acquired by the position information acquisition unit; and a projector device including a display optical element that displays the projection image generated by the projection image generation unit, a projection light source that emits projection light so as to be incident on the display optical element, and a projection lens that projects the projection image emitted from the display optical element to the corresponding part.

According to the projection mapping apparatus, it is possible to generate the projection image which corresponds to the surface shape of the corresponding part of the subject and indicates the position of the leading end of the medical instrument in the subject and to project the projection image to the corresponding part of the subject.

According to another aspect of the invention, in the projection mapping apparatus, the leading end position image acquisition unit acquires, as the leading end position image, a transmission image from a transmission image capture device that captures the transmission image of the corresponding part of the subject. With this configuration, it is possible to project the projection image generated on the basis of a transmission image to the corresponding part of the subject. Therefore, a doctor can insert a medical instrument, without averting the eyes from the subject (without seeing the transmitted light image on a separate monitor).

According to still another aspect of the invention, the projection mapping apparatus further includes a leading end position image generation unit that generates the leading end position image on the basis of the position of the leading end acquired by the position information acquisition unit and a known internal structure of the subject. The leading end position image acquisition unit acquires the leading end position image from the leading end position image generation unit. With this configuration, it is possible to acquire the leading end position image indicating the position of the leading end of the medical instrument in the subject, without acquiring a transmitted light image.

According to yet another aspect of the invention, in the projection mapping apparatus, the position information acquisition unit acquires the position of the leading end on the basis of the transmission image and a known internal structure of the subject. With this configuration, it is possible to acquire the exact position of the leading end of the medical instrument in the subject from the transmitted light image which has been actually captured.

According to still yet another aspect of the invention, in the projection mapping apparatus, the medical instrument is inserted along a known path in the subject and the position information acquisition unit acquires an amount of insertion of the medical instrument into the subject, compares the amount of insertion with the known path, and acquires the position of the leading end on the basis of a comparison result. With this configuration, it is possible to simply acquire the position of the leading end of the medical instrument in the subject.

According to yet still another aspect of the invention, in the projection mapping apparatus, an acceleration sensor and a gyro sensor are provided at the leading end of the medical instrument and the position information acquisition unit detects a moving direction and an amount of movement of the leading end of the medical instrument from an insertion position where the medical instrument is inserted into the subject, on the basis of outputs from the acceleration sensor and the gyro sensor, and acquires the position of the leading end on the basis of detection results of the moving direction and the amount of movement. With this configuration, it is possible to reliably acquire the position of the leading end of the medical instrument in the subject even in a case in which the position of the leading end of the medical instrument is freely moved in the subject.

According to still yet another aspect of the invention, in the projection mapping apparatus, an imaging unit is provided at the leading end of the medical instrument. The projection mapping apparatus further includes an insertion path information acquisition unit that acquires insertion path information indicating an insertion path of the leading end of the medical instrument in the subject on the basis of an image captured by the imaging unit. The position information acquisition unit acquires the position of the leading end on the basis of an insertion position where the medical instrument is inserted into the subject and the insertion path information acquired by the insertion path information acquisition unit. With this configuration, it is possible to reliably acquire the position of the leading end of the medical instrument in the subject even in a case in which the position of the leading end of the medical instrument is freely moved in the subject.

According to yet still another aspect of the invention, the projection mapping apparatus further includes: a switching control unit that switches a wavelength of the measurement light emitted from the light source to the subject before the distance image is generated; and a light source control unit that controls the light source such that the light source emits the measurement light with a wavelength at which intensity is the highest among the measurement light components with each wavelength which are received by the distance image sensor with the switching of the wavelength of the measurement light by the switching control unit. In a case in which the light source irradiates the subject with the measurement light with the wavelength at which intensity is the highest, the distance image generation unit generates the distance image. With this configuration, it is possible to improve the accuracy of determining the distance to the subject based on the distance image or the accuracy of determining the shape of the subject.

According to still yet another aspect of the invention, in the projection mapping apparatus, the light source includes a plurality of light source units that irradiate the subject with the measurement light components with different wavelengths. The switching control unit switches the light source units that emit the measurement light. The light source control unit performs control such that the light source unit that emits the measurement light with the wavelength at which intensity is the highest irradiates the subject with the measurement light. With this configuration, it is possible to improve the accuracy of determining the distance to the subject based on the distance image or the accuracy of determining the shape of the subject.

According to yet still another aspect of the invention, the projection mapping apparatus further includes: a projection range acquisition unit that acquires a projection range of the projection image projected to the subject, on the basis of a focal length of the projection lens, a distance to the subject which is indicated by the distance image generated by the distance image generation unit, and the projection image generated by the projection image generation unit; and a distance image generation control unit that sets a generation range in which the distance image generation unit generates the distance image in correspondence with the projection range acquired by the projection range acquisition unit. With this configuration, it is not necessary to generate the distance image in the entire range of the subject and it is possible to reduce the amount of calculation required for a distance image generation process.

According to still yet another aspect of the invention, in the projection mapping apparatus, the distance image generation unit acquires, from the distance image sensor, the received light signal indicating distance information corresponding to a time of flight of the measurement light which is emitted from the light source, is reflected from the subject, and is incident on the distance image sensor and generates the distance image on the basis of the distance information.

According to yet still another aspect of the invention, in the projection mapping apparatus, the projection image generation unit recognizes the surface shape of the corresponding part on the basis of a shape of the subject detected from the distance image and the position of the leading end acquired by the position information acquisition unit, transforms the leading end position image to a shape fitted to the corresponding part on the basis of a recognition result of the surface shape, and generates the projection image. With this configuration, a projection image corresponding to the surface shape of the corresponding part of the subject is generated.

According to still yet another aspect of the invention, in the projection mapping apparatus, the projection image generation unit decides a display position and a size of the projection image displayed on the display optical element as a display position and a size of the projection image projected so as to overlap the corresponding part, on the basis of a distance from the projector device to the corresponding part which is determined by the distance image and the position of the leading end and focal length information of the projection lens. The display optical element displays the projection image at the display position and in the size decided by the projection image generation unit. With this configuration, it is possible to project the projection image so as to overlap the corresponding part.

The projection mapping apparatus according to the invention can project the projection image indicating the position of the leading end of the medical instrument inserted into the subject in response to a change in the position or posture of the subject.

BRIEF DESCRIPTION OF THE DRAWINGS

FIGS. 26A and 26B are a diagram illustrating the setting of the generation range of distance image data by a distance image generation control unit.

DESCRIPTION OF THE PREFERRED EMBODIMENTS

Figure 1:
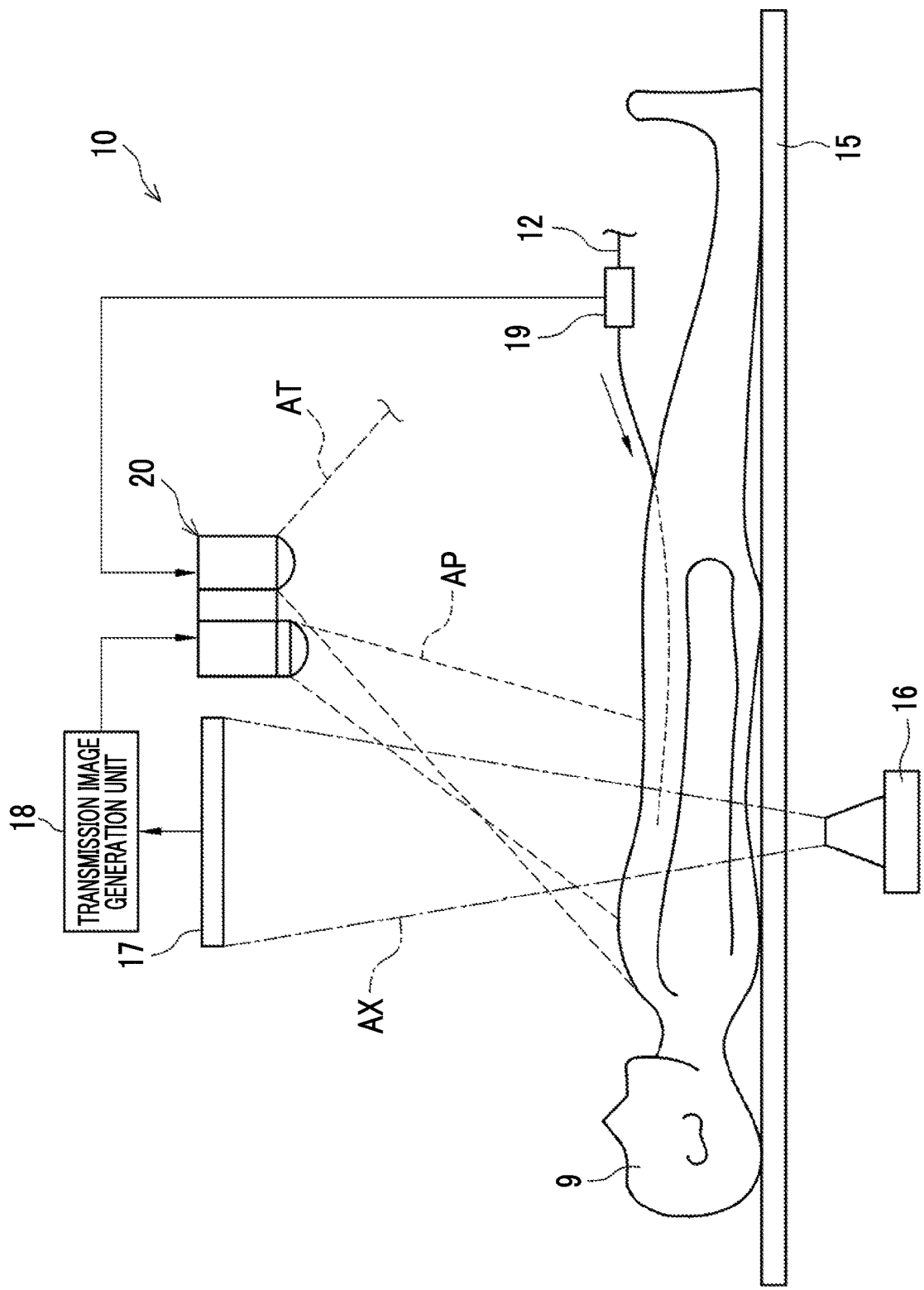
FIG. 1 is a diagram schematically illustrating a surgical support system including a projection mapping apparatus according to the invention.

Surgical Support System (Projection Mapping Apparatus) According to First Embodiment FIG. 1 is a diagram schematically illustrating a surgical support system 10 including a projection mapping apparatus according to the invention. As illustrated in FIG. 1, in a case in which a catheter 12 corresponding to a medical instrument according to the invention is inserted into the body of a patient 9 that is a subject according to the invention, the surgical support system 10 projects an image indicating the position of a leading end of the catheter 12 to a corresponding part of the patient 9 corresponding to the position of the leading end in the body of the patient 9. The term "corresponding part" is a part in which the leading end of the catheter 12 (medical instrument) is located in the body of the patient 9.

The surgical support system 10 includes a table 15 on which the patient 9 lies, an X-ray tube 16 that is provided below the table 15, an X-ray flat panel detector (FPD) 17 that is provided above the table 15, a transmission image generation unit 18, a feed amount sensor 19, and a projection mapping apparatus 20 according to the invention. Hereinafter, the projection mapping apparatus is appropriately abbreviated to a "PM apparatus".

The X-ray tube 16, the X-ray flat panel detector 17, and the transmission image generation unit 18 correspond to a transmission image capture device according to the invention that captures a transmission image. The X-ray tube 16 irradiates the patient 9 with X-rays through the table 15. In FIG. 1, letters AX indicate an X-ray irradiation range. The X-ray flat panel detector 17 detects X-rays transmitted through the table 15 and the patient 9 and outputs a detection signal to the transmission image generation unit 18.

The transmission image generation unit 18 generates, as a transmission image according to the invention, transmission image data 22 (see FIG. 5) which is an X-ray image on the basis of the detection signal input from the X-ray flat panel detector 17 and outputs the transmission image data 22 to the PM apparatus 20. Since the X-ray tube 16, the X-ray flat panel detector 17, and the transmission image generation unit 18 are known techniques, the detailed description thereof will be omitted.

In addition, the X-ray tube 16 and the X-ray flat panel detector 17 can be moved relative to the table 15 by a relative movement mechanism (not illustrated). Therefore, the emission of X-rays by the X-ray tube 16, the detection of X-rays by the X-ray flat panel detector 17, and the generation of the transmission image data 22 (see FIG. 5) by the transmission image generation unit 18 are repeated while the X-ray tube 16 and the X-ray flat panel detector 17 are being moved relative to the table 15 (patient 9) to obtain the transmission image data 22 of each part of the patient 9.

In this example, the X-ray tube 16 and the X-ray flat panel detector 17 are moved relative to the table 15 (patient 9) according to the position of the leading end of the catheter 12 in the body of the patient 9 such that the transmission image data 22 of the corresponding part is always obtained while the catheter 12 is being inserted. In addition, the relative movement by the relative movement mechanism may be manually performed by, for example, a medical staff member or relative movement corresponding to the position of the leading end of the catheter 12 may be automatically performed by the relative movement mechanism on the basis of the acquisition result of the position of the leading end of the catheter 12 in the body of the patient 9, which will be described below.

The feed amount sensor 19 is a sensor that detects the amount of feed of the catheter 12. It is possible to acquire the amount of insertion of the catheter 12 into the body of the patient 9 on the basis of the detection result of the feed amount sensor 19. The feed amount sensor 19 outputs the detection result of the amount of feed of the catheter 12 to the PM apparatus 20.

The PM apparatus 20 has a function of generating distance image data 23 (see FIG. 6) of the patient 9 on the table 15 and a function of generating projection image data 24 (see FIG. 6) that indicates the position of the leading end of the catheter 12 in the body of the patient 9 and corresponds to the surface shape of the corresponding part and projecting a projection image based on the projection image data 24 to the corresponding part of the patient 9. In FIG. 1, letters AT indicate a generation range in which the distance image data 23 is generated. In FIG. 1, letters AP indicate a projection range (irradiation range) of the projection image.

Configuration of PM Apparatus According to First Embodiment

Figure 2:
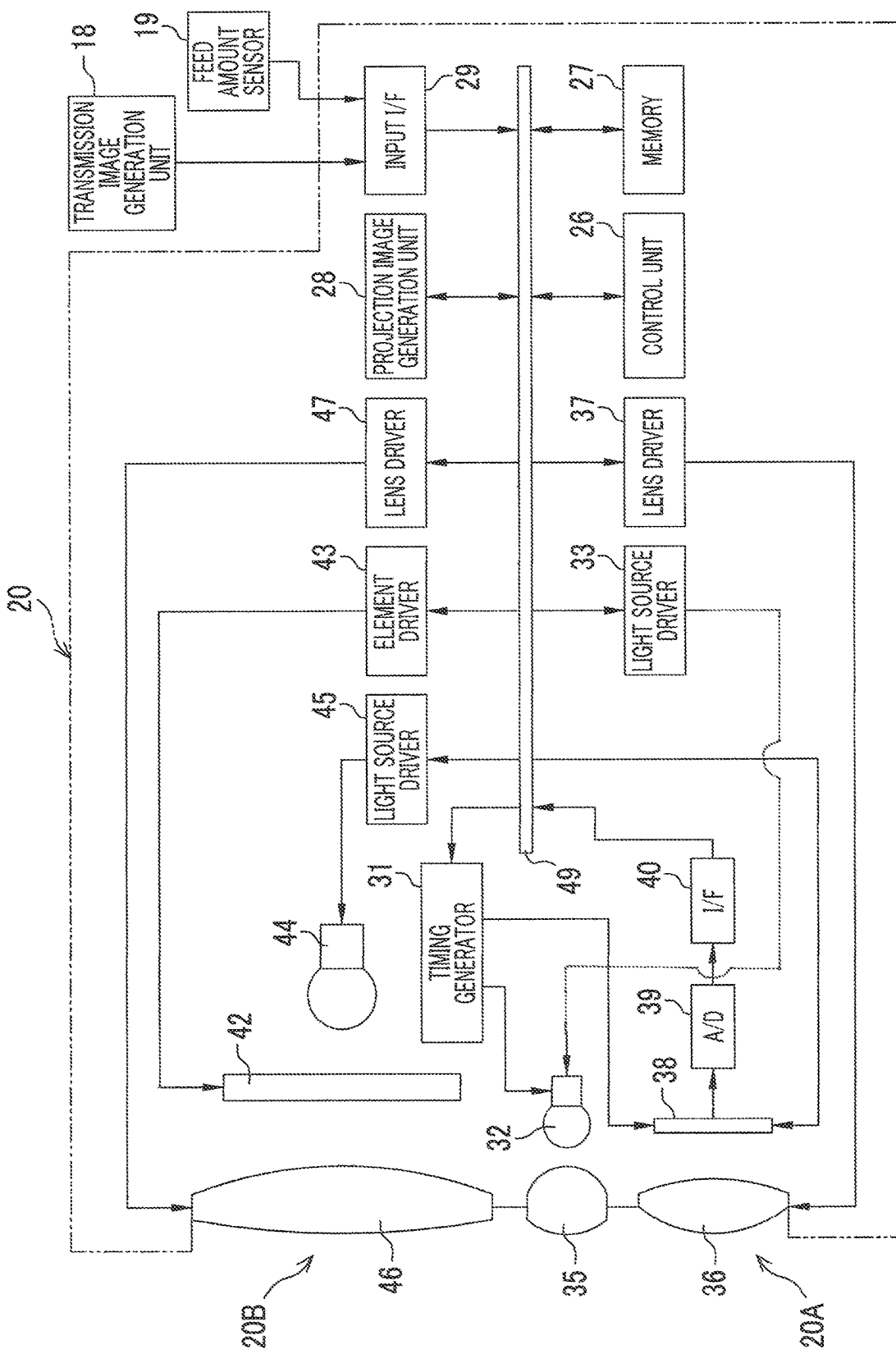
FIG. 2 is a block diagram illustrating the configuration of a projection mapping apparatus according to a first embodiment.

FIG. 2 is a block diagram illustrating the configuration of the PM apparatus 20 according to the first embodiment. The PM apparatus 20 includes a distance image acquisition device 20A related to the generation of the distance image data 23, a projector device 20B that projects the projection image based on the projection image data 24, a control unit 26, a memory 27, a projection image generation unit 28, and an input interface (I/F) 29.

The distance image acquisition device 20A acquires a distance image using a pulsed light detection method and includes a timing generator 31, a light emitting diode (LED) light source 32, a light source driver 33, a projection lens 35, a focus lens 36, a lens driver 37, a distance image sensor 38, an analog-to-digital (AD) converter 39 that is represented by "A/D" in FIG. 2, and an interface circuit 40 that is represented by "I/F" in FIG. 2.

The timing generator 31 outputs a timing signal to each of the LED light source 32 and the distance image sensor 38 under the control of the control unit 26.

The LED light source 32 corresponds to a light source according to the invention and emits pulsed light with a constant pulse width in synchronization with the timing signal input from the timing generator 31. The pulsed light corresponds to measurement light according to the invention. In this example, the pulsed light is near-infrared light. The light source driver 33 controls the driving of the LED light source 32 under the control of the control unit 26. Light sources other than the LED can be used as the light source according to the invention. In addition, the measurement light according to the invention is not limited to the pulsed light which is near-infrared light.

The projection lens 35 emits the pulsed light from the LED light source 32 to the patient 9 on the table 15. In a case in which the patient 9 is irradiated with the pulsed light, the focus lens 36 focuses pulsed light reflected from the patient 9 on the distance image sensor 38. The lens driver 37 controls, for example, the focus of the focus lens 36 through a lens driving unit (not illustrated). In this example, the position of the PM apparatus 20 and the table 15 is substantially fixed. Therefore, focus adjustment is performed for the patient 9 on the table 15 in advance.

The distance image sensor 38 includes a complementary metal-oxide semiconductor (CMOS) driver having, for example, a vertical driver and a horizontal driver and a CMOS image sensor that is driven by the timing generator 31. However, the distance image sensor 38 is not limited to the CMOS type and may be an XY-address-type image sensor or a charge coupled device (CCD) image sensor.

In the distance image sensor 38, a plurality of light receiving elements (photodiodes) are two-dimensionally arranged. A bandpass filter that transmits only the wavelength band of the pulsed light which is near-infrared light emitted from the LED light source 32 or a visible light cut filter that cuts visible light is provided on the incident surface side of the plurality of light receiving elements. Therefore, the plurality of light receiving elements of the distance image sensor 38 function as pixels that are sensitive to the pulsed light which is near-infrared light.

The exposure period (the exposure time and exposure timing) of the distance image sensor 38 is controlled by the timing signal input from the timing generator 31 in synchronization with the emission of pulsed light from the LED light source 32. Charge corresponding to the amount of pulsed light incident for the exposure period is accumulated in each light receiving element of the distance image sensor 38. As such, in the pulsed light detection method, as the distance (time of flight) to the patient 9 is reduced, the amount of exposure increases. On the contrary, as the distance (time of flight) to the patient 9 increases, the amount of exposure is reduced. Therefore, it is possible to measure the distance to the patient 9 according to the amount of exposure. In this example, the subject is the patient 9 and the surgical support system 10 is installed in the hospital. It is assumed that a difference in the reflectance of the subject or the influence of external light is not considered.

A received light signal (also referred to as a pixel signal which is an analog signal corresponding to the charge accumulated in each pixel) corresponding to the amount of incident pulsed light reflected from the patient 9 is read out from the distance image sensor 38. The received light signal indicates distance information corresponding to the time of flight of the pulsed light which has been reflected from the patient 9 and then incident on the distance image sensor 38.

The AD converter 39 converts the received light signal read out from the distance image sensor 38 into a digital signal and outputs the digital signal to the interface circuit 40. In some cases, the CMOS image sensor includes the AD converter. In this case, the AD converter 39 can be omitted. The interface circuit 40 functions as an image input controller and outputs the digital signal input from the AD converter 39 to the control unit 26. In this way, the distance image data 23 (see FIG. 3) is generated by the control unit 26, which will be described below.

The projector device 20B is a so-called a single-panel liquid crystal projector and includes a display optical element (also referred to as a light modulation element) 42, an element driver 43, an LED light source 44, a light source driver 45, a projection lens 46, and a lens driver 47.

The display optical element 42 is, for example, a transmissive liquid crystal panel including color filters of a plurality of colors or an element with a color-filterless structure obtained by combining a dichroic mirror, a microlens array, and a transmissive monochrome liquid crystal panel. In the element with a color-filterless structure, for example, three types of dichroic mirrors that reflect red (R) light, green (G) light, and blue (B) light disperse white light into three RGB light components such that the three color light components are incident on the microlens array on the liquid crystal panel at different angles. Then, the three color light components are incident on an R pixel, a G pixel, and a B pixel of the liquid crystal panel by the microlens array. In this way, it is possible to display a color image.

The projector device 20B is not limited to the single-panel liquid crystal projector and may be a known three-panel liquid crystal projector including a color separation optical system and a plurality of liquid crystal panels. In addition, the projector device 20B is not limited to the transmissive liquid crystal type and may be various other types, such as a reflective liquid crystal display type or a reflective display type using a digital mirror device (DMD).

The element driver 43 controls the display optical element 42 under the control of the control unit 26 such that the projection image data 24 generated by the projection image generation unit 28 which will be described below is displayed.

The LED light source 44 corresponds to a projection light source according to the invention and emits white light (projection light according to the invention) so as to be incident on the display optical element 42 from the rear side (a side opposite to the projection lens 46) of the display optical element 42. Then, the image light of the projection image based on the projection image data 24 is emitted from the display optical element 42. The light source driver 45 controls the driving of the LED light source 44 under the control of the control unit 26. In addition, light sources other than the LED can be used as the projection light source according to the invention. In a case in which a display optical element that sequentially projects R light, B light, and G light in a time division manner, such as a DMD, is used, a light source that sequentially emits R light, B light, and G light to the display optical element in a time division manner is used as the projection light source. That is, light other than white light, such as R light, B light, and G light, can be used as the projection light according to the invention.

The projection lens 46 projects the image light of the projection image emitted from the display optical element 42 to the patient 9. The lens driver 47 controls, for example, the focus of the projection lens 46 through a lens driving unit (not illustrated). In this example, since the position of the PM apparatus 20 and the table 15 is substantially fixed, for example, focus adjustment is performed for the patient 9 on the table 15 in advance.

The control unit 26 is connected to, for example, the timing generator 31, the light source driver 33, the lens driver 37, the distance image sensor 38, the interface circuit 40, the element driver 43, the light source driver 45, and the lens driver 47 through a data bus 49. The control unit 26 includes, for example, various arithmetic units and processing units including a central processing unit (CPU) and a storage unit and executes a control program or data read out from the memory 27 to generally control the overall operation or process of the PM apparatus 20. In addition, the control unit 26 generates and acquires data or information used for the generation of the projection image data 24 by the projection image generation unit 28, which will be described in detail below (see FIG. 3).

In addition to the control program used by the control unit 26 to perform processes, the memory 27 stores internal structure information 50 (corresponding to an internal structure according to the invention) used for the acquisition of information related to the position of the leading end of the catheter 12 in the body of the patient 9 and insertion path information 51 (corresponding to a known path according to the invention), which will be described in detail below (see FIG. 3).

The projection image generation unit 28 generates the projection image data 24 which is the projection image according to the invention on the basis of data or information input from the control unit 26 under the control of the control unit 26, which will be described in detail below.

The input I/F 29 is a communication interface that is connected to the transmission image generation unit 18 or the feed amount sensor 19 wirelessly or in a wired manner. The input I/F 29 acquires the transmission image data 22 from the transmission image generation unit 18 and acquires the detection result of the amount of feed from the feed amount sensor 19. Then, the input I/F 29 outputs the transmission image data 22 and the detection result of the amount of feed to the control unit 26.

Figure 3:
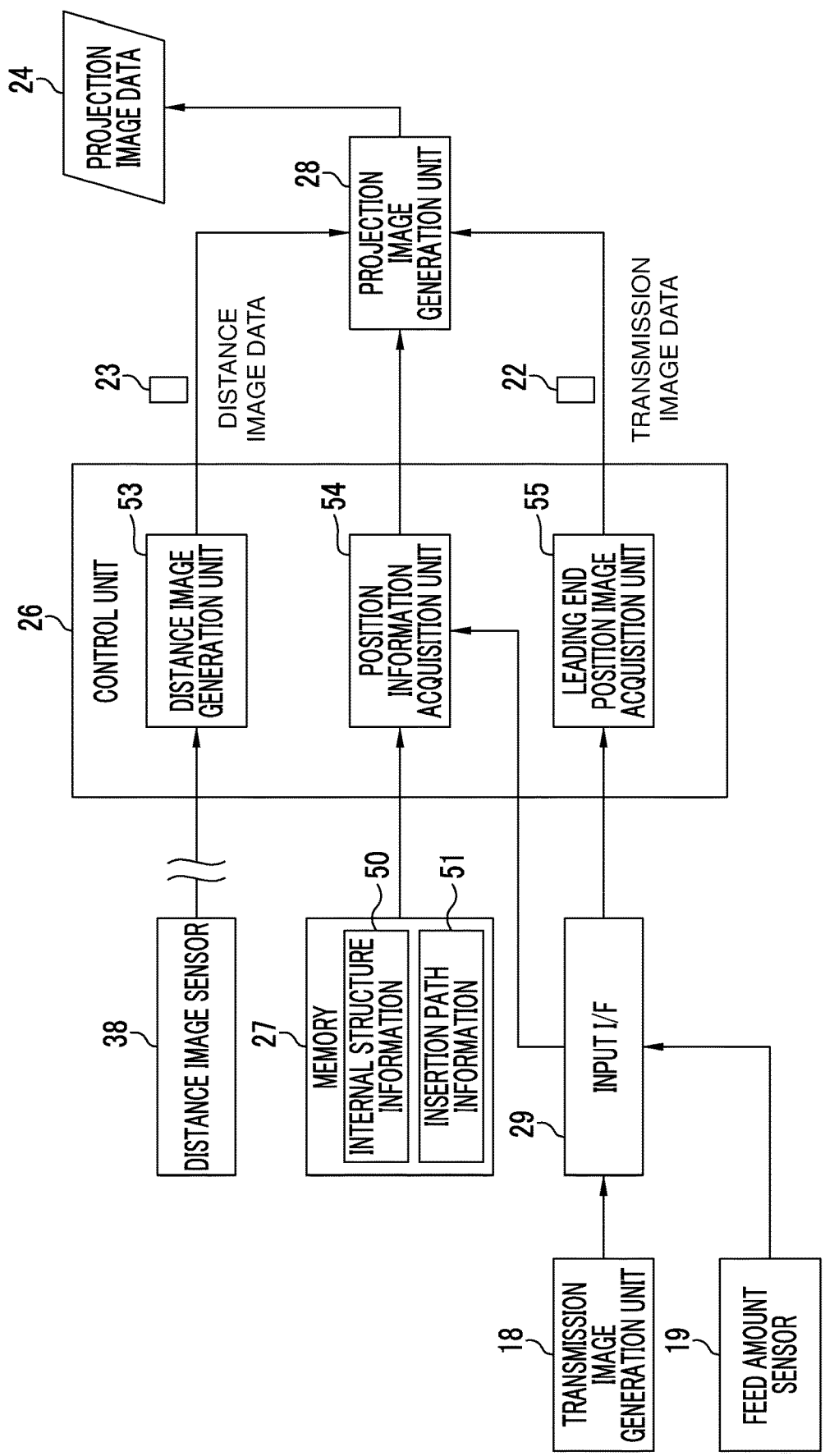
FIG. 3 is a functional block diagram illustrating a control unit according to the first embodiment.

FIG. 3 is a functional block diagram illustrating the control unit 26 in the first embodiment. In FIG. 3, the data bus 49 is not illustrated. As illustrated in FIG. 3, the control unit 26 executes the program or data read out from the memory 27 to function as a distance image generation unit 53, a position information acquisition unit 54, and a leading end position image acquisition unit 55.

The distance image generation unit 53 generates the distance image data 23 on the basis of the digital signal input from the interface circuit 40. As described above, the amount of light received by each light receiving element of the distance image sensor 38 varies depending on the distance to the patient 9. Therefore, the distance image data 23 is data having information about the distance from the distance image sensor 38 to the patient 9 for each pixel, that is, data having information about the distance to each point on the body surface of the patient 9, instead of the color or tone of general two-dimensional image data. The distance image data 23 indicates the distance to the patient 9 and the surface shape of the patient 9. The distance image generation unit 53 outputs the generated distance image data 23 to the projection image generation unit 28.

The position information acquisition unit 54 acquires the position of the leading end of the catheter 12 inserted into the body of the patient 9. The term "the position of the leading end" also includes information related to the direction (orientation) of the leading end.

In this embodiment, the position information acquisition unit 54 can select a method that acquires the position of the leading end of the catheter 12 using the transmission image data 22 acquired through the input I/F 29 and a method that acquires the position of the leading end of the catheter 12 using the detection result of the amount of feed by the feed amount sensor 19 acquired through the input I/F 29. The user operates, for example, an operation unit (not illustrated) to select one of the methods.

In a case in which the method that acquires the position of the leading end of the catheter 12 using the transmission image data 22 is selected, the position information acquisition unit 54 acquires the position of the leading end of the catheter 12 on the basis of the transmission image data 22 and the internal structure information 50 which is stored in the memory 27 in advance.

Figure 4:
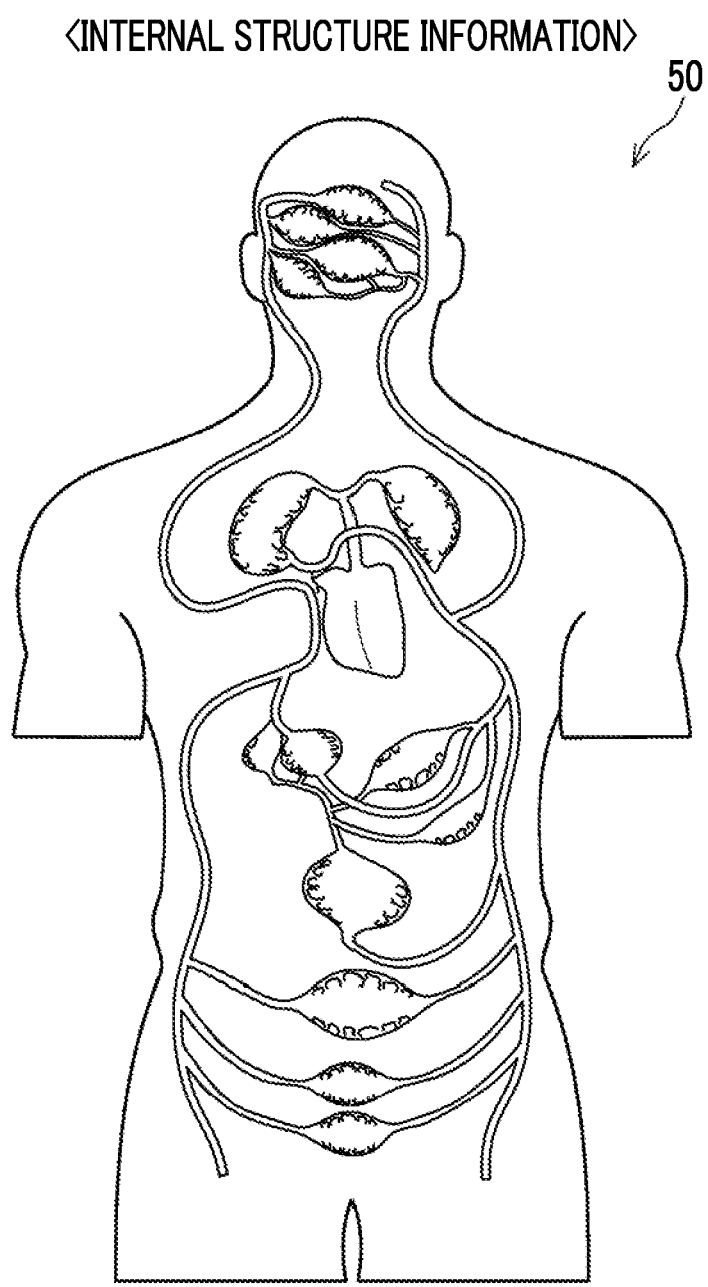
FIG. 4 is a diagram illustrating an example of internal structure information according to the first embodiment.
Figure 5:
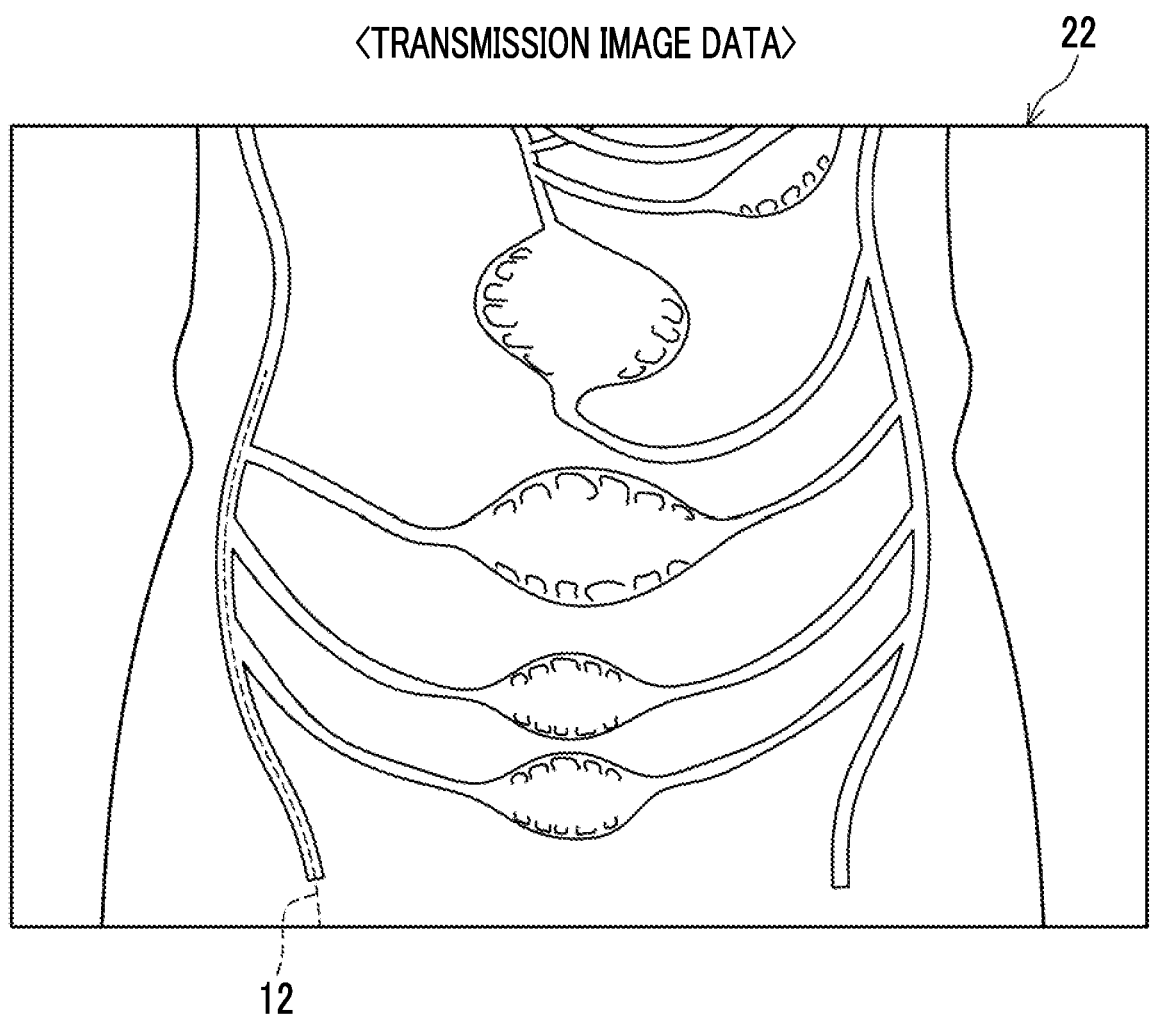
FIG. 5 is a diagram illustrating an example of transmission image data.

FIG. 4 is a diagram illustrating an example of the internal structure information 50. FIG. 5 is a diagram illustrating an example of the transmission image data 22. As illustrated in FIG. 4, the internal structure information 50 used in a case in which the catheter 12 is inserted into the blood vessel in the body of the patient 9 is information indicating the structure of the blood vessel in the body of the patient 9. The internal structure information 50 can be acquired by performing magnetic resonance imaging (MRI) or computed tomography (CT) for the patient 9 in advance. The structure of the blood vessel in the body of the patient 9 is obtained with reference to the internal structure information 50.

As illustrated in FIG. 5, the transmission image data 22 of the corresponding part of the patient 9 includes an image of the leading end of the catheter 12 and an image of the blood vessel in the vicinity of the position of the leading end of the catheter 12. Here, since the transmission image data 22 is an X-ray image as described above, it is possible to capture the image of the blood vessel on the transmission image data 22 by injecting a contrast medium that does not transmit X-rays into the patient 9 in advance.

Returning to FIG. 3, the position information acquisition unit 54 extracts the image of the blood vessel from the transmission image data 22 using a known method (for example, see JP2011-161091A) and compares the image of the blood vessel in the transmission image data 22 with the blood vessel structure of the patient 9 indicated by the internal structure information 50 using a pattern matching method. In this way, the position information acquisition unit 54 can recognize where the blood vessel of the transmission image data 22 is located in the body of the patient 9.

In addition, a known method is used to extract the image of the catheter 12 from the transmission image data 22 (for example, see paragraph 0005 in JP2007-229473A). Therefore, the position information acquisition unit 54 can acquire the position of the leading end of the catheter 12 inserted into the body of the patient 9 on the basis of the recognition result of the blood vessel and the position of the leading end of the catheter 12 in the transmission image data 22.

In contrast, in a case in which the method that acquires the position of the leading end of the catheter 12 using the detection result of the amount of feed by the feed amount sensor 19 is selected, the position information acquisition unit 54 acquires the position of the leading end of the catheter 12 on the basis of the detection result and the insertion path information 51 stored in advance in the memory 27.

The insertion path information 51 used in a case in which the catheter 12 is inserted into the blood vessel in the body of the patient 9 is information indicating the insertion position of the catheter 12 into the blood vessel and the path of the blood vessel through which the catheter 12 reaches a target position. The doctor decides the insertion path information 51 in advance on the basis of, for example, the internal structure information 50 and stores the insertion path information 51 in the memory 27.

The position information acquisition unit 54 compares the detection result of the amount of feed by the feed amount sensor 19 with the insertion path information 51 to recognize the position of the leading end of the catheter 12 on the path of the blood vessel in the insertion path information 51. Since the position where the blood vessel of the insertion path information 51 is located in the body of the patient 9 is known, the position information acquisition unit 54 can acquire the position of the leading end of the catheter 12 inserted into the body of the patient 9 from the position of the leading end of the catheter 12 on the path of the blood vessel.

After acquiring the position of the leading end of the catheter 12 in the body of the patient 9 using any of the above-mentioned methods, the position information acquisition unit 54 outputs leading end position information indicating the position of the leading end to the projection image generation unit 28.

The leading end position image acquisition unit 55 acquires the transmission image data 22 from the transmission image generation unit 18 through the input I/F 29 and outputs the transmission image data 22 to the projection image generation unit 28. As illustrated in FIG. 5, since the transmission image data 22 includes the image of the leading end of the catheter 12 and the image of the blood vessel in the vicinity of the position of the leading end of the catheter 12, the transmission image data 22 is leading end position image according to the invention indicating the position of the leading end of the catheter 12 in the body of the patient 9. In addition, it is preferable that the leading end position image according to the invention is an image including at least information about the inside of the body of the patient 9 at the position of the leading end [for example, organs, muscle, bones, joints, and the blood vessels] or an image indicated by the information about the inside of the body.

Figure 6:
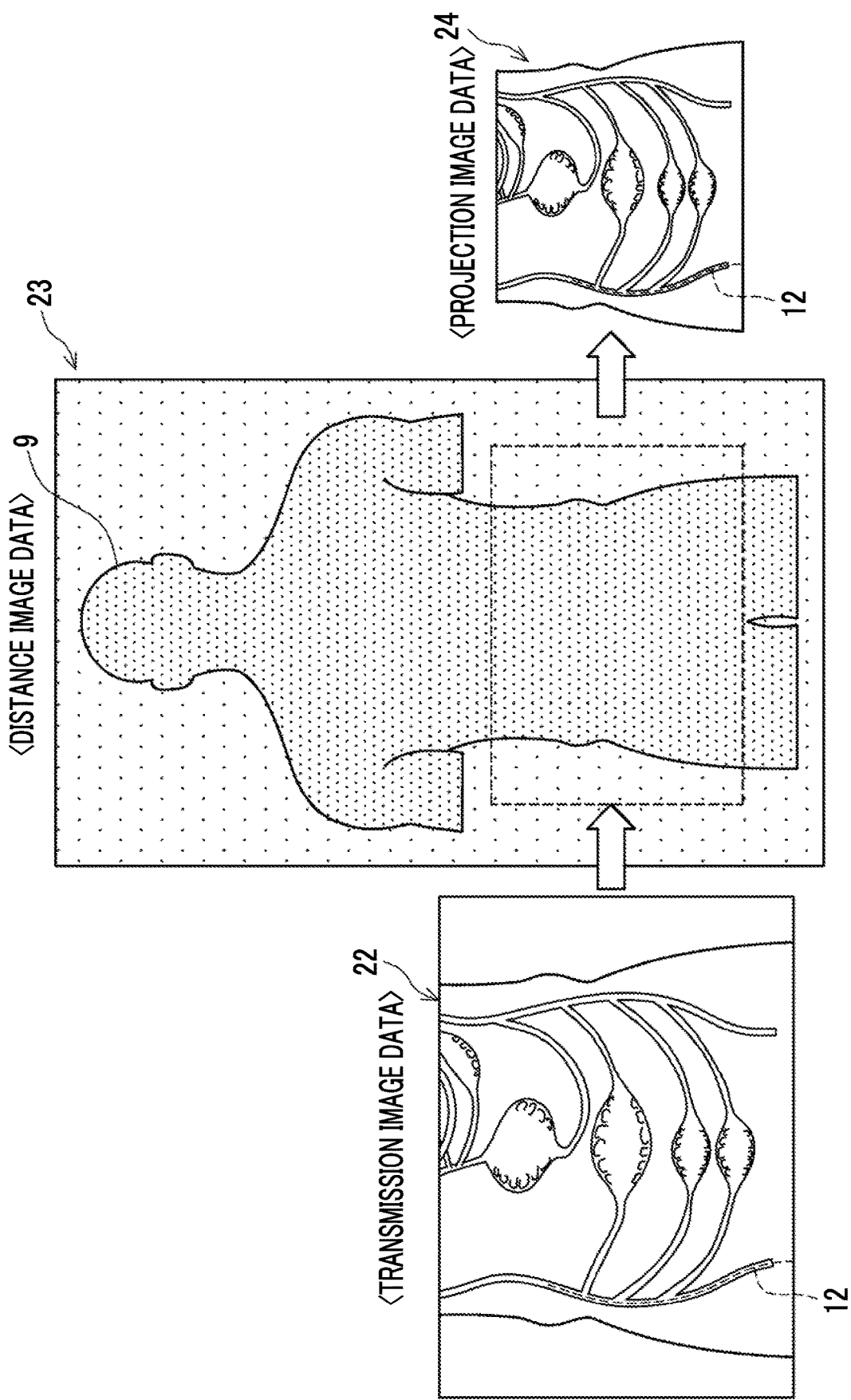
FIG. 6 is a diagram illustrating a projection image data generation process performed by a projection image generation unit according to the first embodiment.

FIG. 6 is a diagram illustrating the process of generating the projection image data 24 by the projection image generation unit 28 according to the first embodiment. As illustrated in FIG. 6, the projection image generation unit 28 generates the projection image data 24 that is to be projected to the patient 9 and is displayed on the display optical element 42 from the transmission image data 22 input from the leading end position image acquisition unit 55.

Specifically, the projection image generation unit 28 recognizes the surface shape of the corresponding part of the patient 9 (a part of the patient 9 included in a dotted frame in FIG. 6) in which the leading end of the catheter 12 is located on the basis of the distance image data 23 input from the distance image generation unit 53 and the leading end position information input from the position information acquisition unit 54. The surface shape of the corresponding part is the surface shape of the corresponding part of the patient 9 as viewed from the PM apparatus 20. For example, in a case in which the position or posture of the patient changes, the surface shape of the corresponding part recognized by the projection image generation unit 28 changes even though the position of the leading end of the catheter 12 is not moved. Therefore, the surface shape of the corresponding part corresponding to the real-time position or posture of the patient is recognized.

Then, the projection image generation unit 28 transforms the transmission image data 22 to a shape fitted to the corresponding part of the patient 9 on the basis of the recognition result of the surface shape of the corresponding part and generates the projection image data 24. In this example, the projection image generation unit 28 detects a blank region with a substantially uniform density from the transmission image data 22, extracts a region corresponding to the corresponding part of the patient 9 from the transmission image data 22, transforms image data of the extracted region to a shape fitted to the corresponding part of the patient 9, and generates the projection image data 24.

At that time, in this example, since the direction in which an X-ray image is captured by the X-ray flat panel detector 17 is substantially the same as the direction in which the distance image data 23 is captured by the PM apparatus 20, an enlargement and reduction process is mainly performed as the process of transforming the transmission image data 22 into the projection image data 24. In contrast, in a case in which the direction in which an X-ray image is captured by the X-ray flat panel detector 17 is different from the direction in which the distance image data 23 is captured by the PM apparatus 20, for example, a projection transform process is performed in addition to the enlargement and reduction process.

In addition, the projection image generation unit 28 determines the display position and size of the projection image data 24 on the display optical element 42 such that a projection image based on the projection image data 24 is projected so as to overlap the corresponding part of the patient 9, on the basis of the distance from the PM apparatus 20 (projector device 20B) to the corresponding part of the patient 9 which is determined from the distance image data 23 and the leading end position information and information about the focal length of the projection lens 46. Then, the projection image generation unit 28 outputs the projection image data 24 to the element driver 43. Then, the element driver 43 displays the projection image data 24 input from the projection image generation unit 28 on the display optical element 42 in the size and at the position determined by the projection image generation unit 28.

Figure 7:
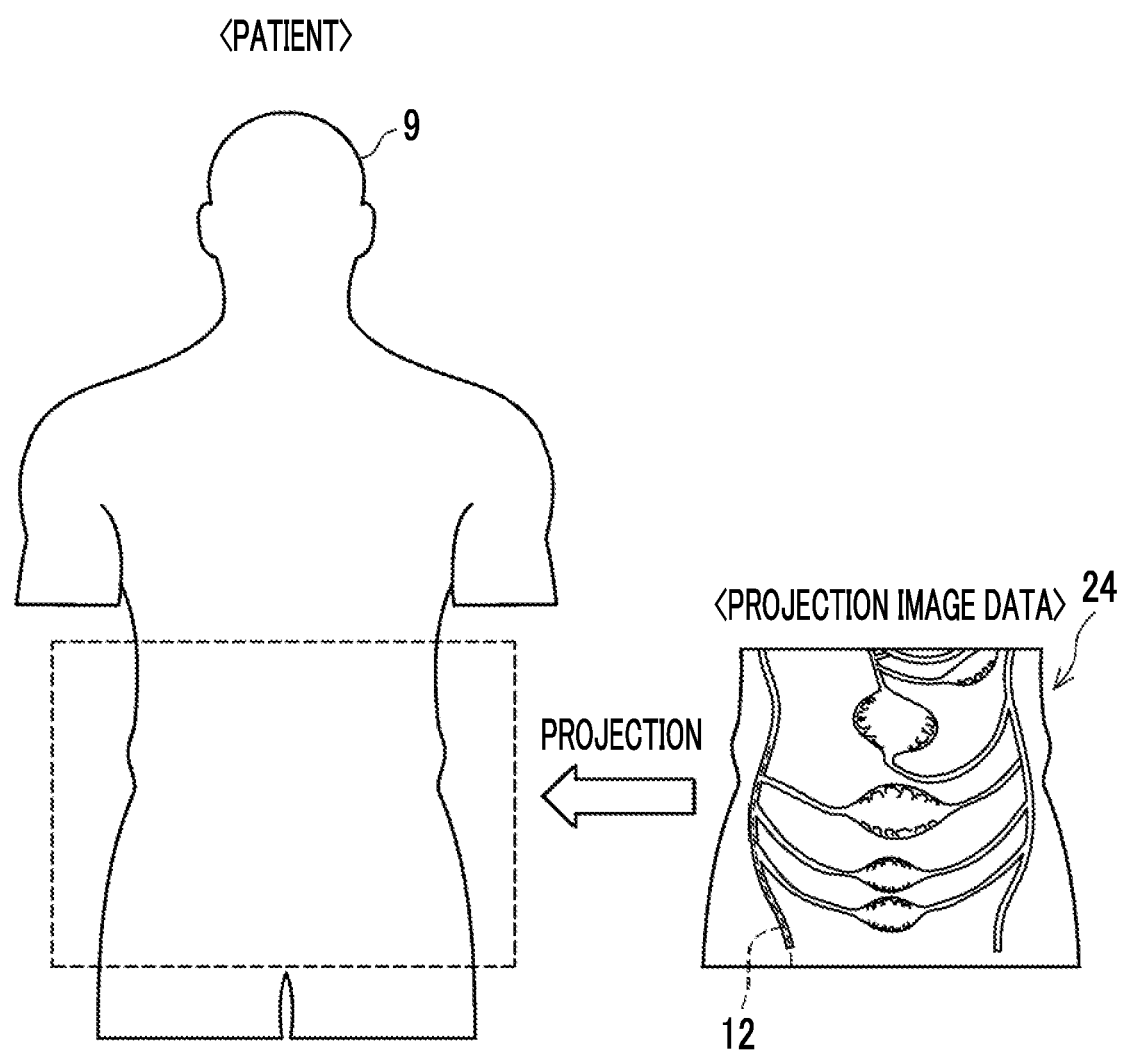
FIG. 7 is a diagram illustrating the projection of a projection image based on projection image data to a patient.
Figure 8:
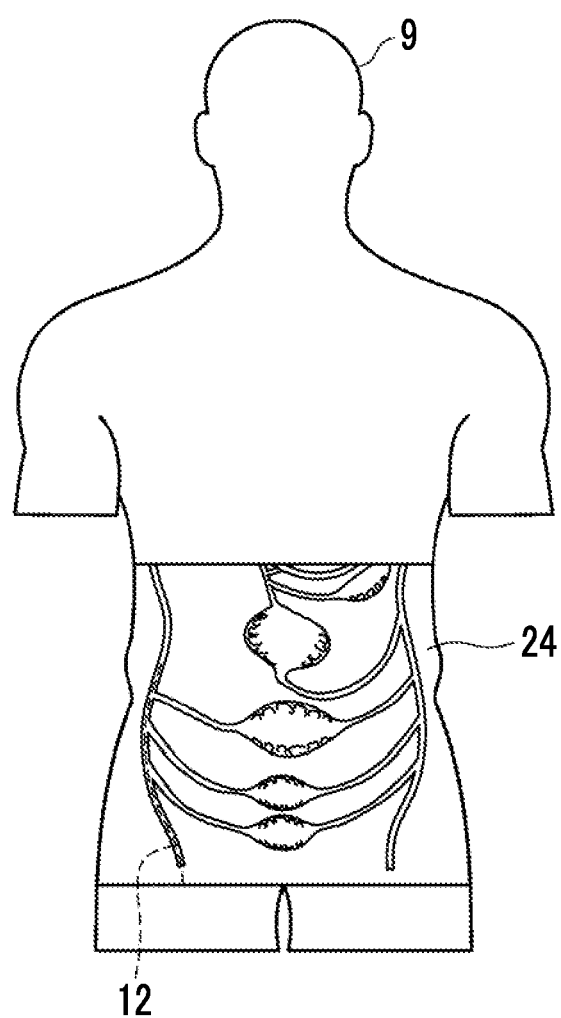
FIG. 8 is a diagram illustrating a state in which the projection image based on the projection image data is projected to the patient.

FIG. 7 is a diagram illustrating the projection of the projection image based on the projection image data 24 to the patient 9. FIG. 8 is a diagram illustrating a state in which the projection image based on the projection image data 24 is projected to the patient 9.

As illustrated in FIG. 7, in a case in which the display optical element 42 displays the projection image data 24, the display optical element 42 modulates white light emitted from the LED light source 44 and image light of the projection image based on the projection image data 24 is projected to the corresponding part of the patient 9. Then, as illustrated in FIG. 8, the projection image based on the projection image data 24, that is, an image indicating the position of the leading end of the catheter 12 in the body of the patient 9 is projected onto the corresponding part of the patient 9.

At that time, the generation of the projection image data 24 and the determination of the display position and size of the projection image data 24 on the display optical element 42 by the projection image generation unit 28 may be performed such that the position of the leading end of the catheter 12 in the projection image is aligned with the actual position of the leading end of the catheter 12 in the body of the patient 9.

Figure 9:
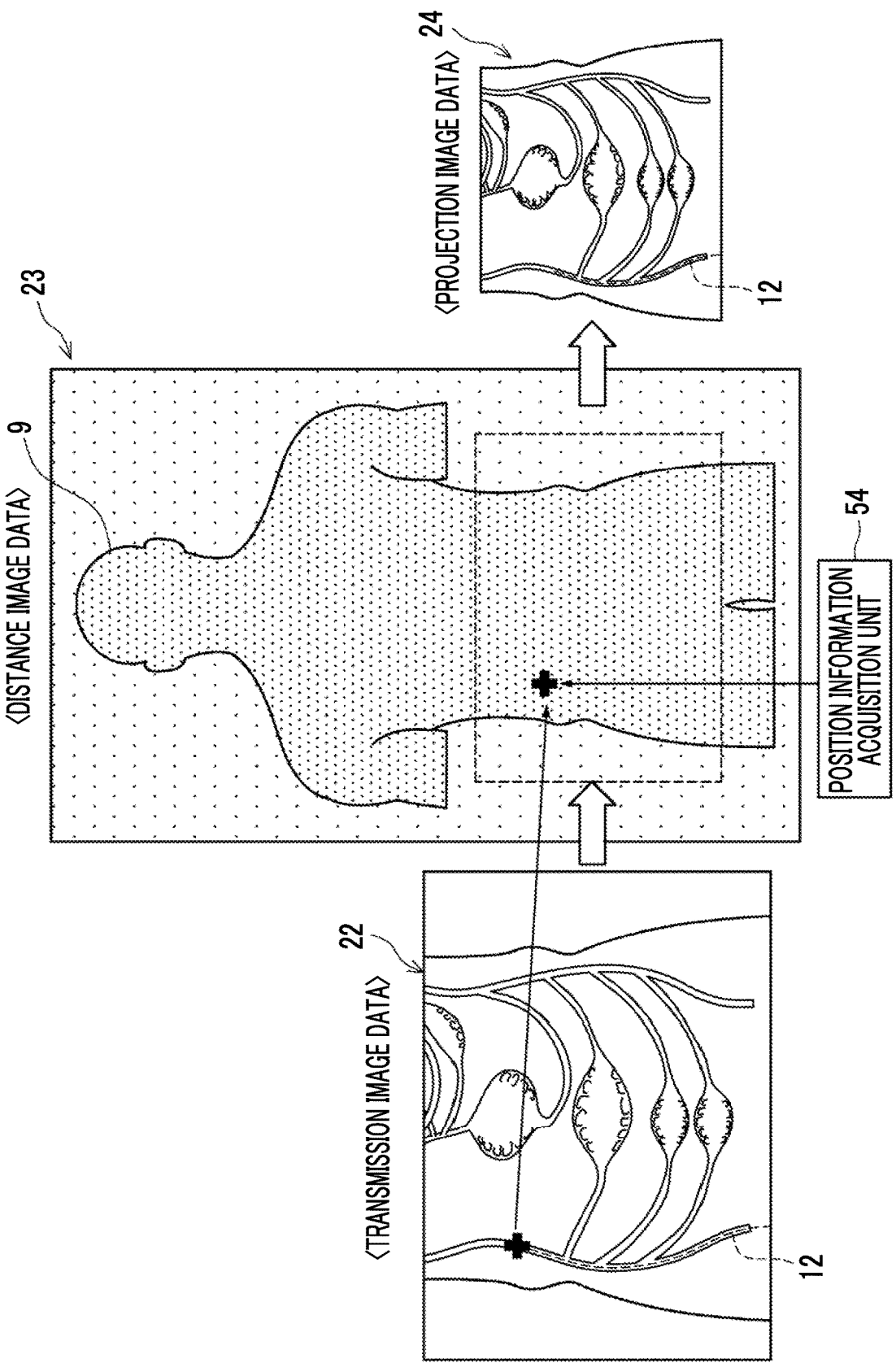
FIG. 9 is a diagram illustrating a modification example of the projection image data generation process performed by the projection image generation unit.

FIG. 9 is a diagram illustrating a modification example of the process of generating the projection image data 24 by the projection image generation unit 28.

As illustrated in FIG. 9, the projection image generation unit 28 contrasts the leading end position information acquired by the position information acquisition unit 54 with the distance image data 23 to acquire the position of the leading end of the catheter 12 (represented by a cross in FIG. 9) inserted into the body of the patient 9 on the distance image data 23. In addition, the projection image generation unit 28 can extract the image of the catheter 12 from the transmission image data 22 to acquire the position of the leading end of the catheter 12 in the transmission image data 22. The projection image generation unit 28 can generate the projection image data 24 and determine the display position and size of the projection image data 24 such that the position of the leading end of the catheter 12 in the transmission image data 22 is aligned with the position of the leading end of the catheter 12 in the body of the patient 9.

The generation of the distance image data 23 by the distance image generation unit 53, the acquisition of the leading end position information by the position information acquisition unit 54, and the acquisition of the transmission image data 22 by the leading end position image acquisition unit 55 are repeatedly performed. With the repetition of the processes, the generation of new projection image data 24 by the projection image generation unit 28 is also repeatedly performed. As a result, the projection image projected to the corresponding part of the patient 9 is updated.

Operation of Surgical Support System According to First Embodiment

Figure 10:
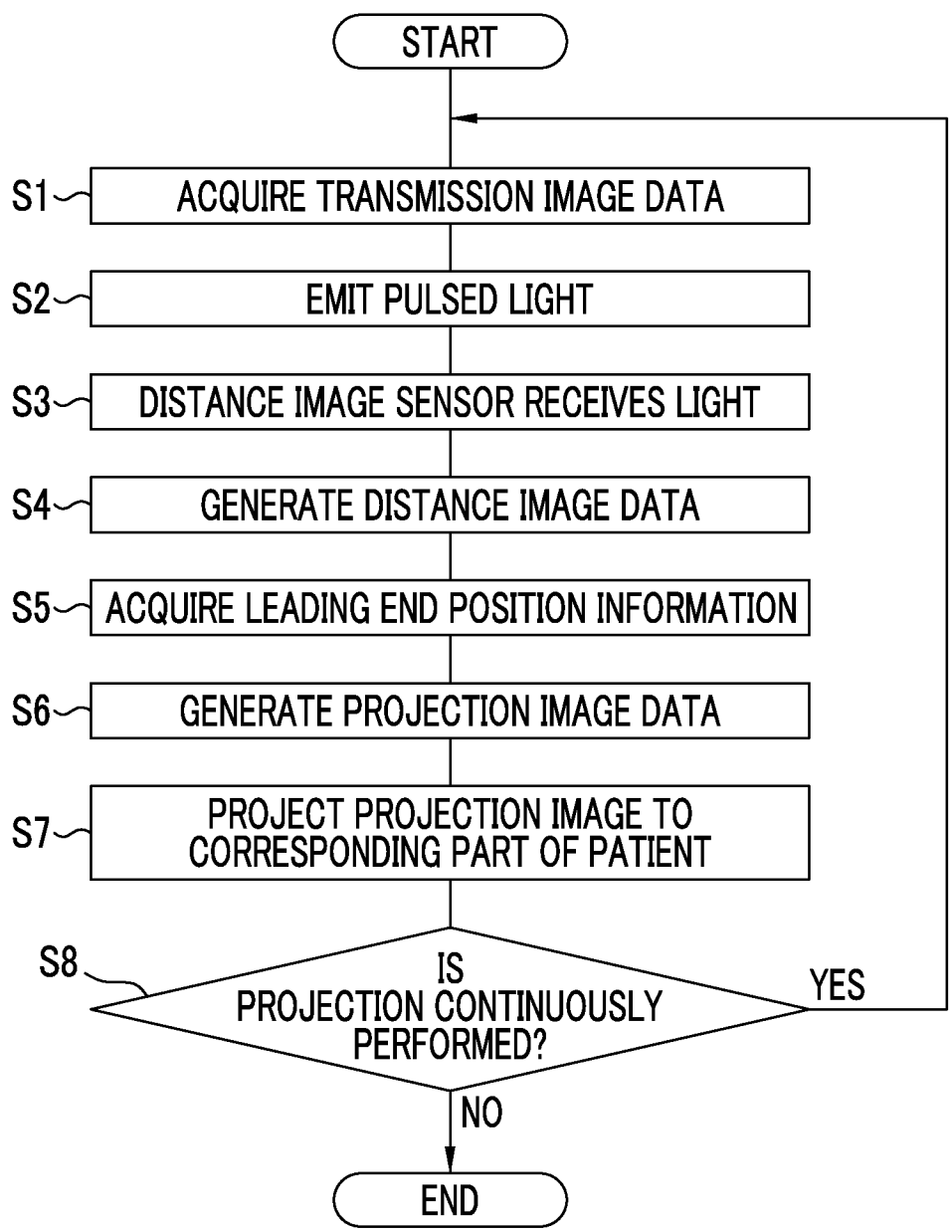
FIG. 10 is a flowchart illustrating the flow of a projection image projection process performed by the projection mapping apparatus of the surgical support system according to the first embodiment.

Next, the operation of the surgical support system 10 with the above-mentioned configuration will be described with reference to FIG. 10. FIG. 10 is a flowchart illustrating the flow of a projection image projection process performed by the PM apparatus 20 of the surgical support system 10 according to the first embodiment. It is assumed that the internal structure information 50 or the insertion path information 51 of the patient 9 is acquired in advance and is stored in the memory 27.

Before the doctor starts to insert the catheter 12 into the blood vessel in the body of the patient 9, each unit of the surgical support system 10 starts. Then, the doctor inserts the catheter 12 into the blood vessel of the patient 9.

In a case in which the surgical support system 10 starts, the X-ray tube 16 irradiates the corresponding part of the patient 9 with X-rays, the X-ray flat panel detector 17 detects X-rays transmitted through the patient 9, and the transmission image generation unit 18 generates the transmission image data 22. The transmission image data 22 generated by the transmission image generation unit 18 is input to the control unit 26 of the PM apparatus 20 through the input I/F 29. Then, the leading end position image acquisition unit 55 of the control unit 26 acquires the transmission image data 22 indicating the position of the leading end of the catheter 12 in the body of the patient 9 and outputs the transmission image data 22 to the projection image generation unit 28 (Step S1).

In addition, in a case in which the surgical support system 10 starts, the control unit 26 of the PM apparatus 20 controls the light source driver 33 such that the LED light source 32 starts to be driven. Then, the LED light source 32 emits pulsed light in synchronization with the timing signal input from the timing generator 31. Then, the pulsed light emitted from the LED light source 32 is emitted to the patient 9 by the projection lens 35 (Step S2).

The pulsed light emitted to the patient 9 is reflected from the body surface of the patient 9 and is then incident on the focus lens 36. The pulsed light is focused on the distance image sensor 38 by the focus lens 36. Then, the distance image sensor 38 receives the pulsed light reflected from the patient 9 (Step S3). Then, a received light signal corresponding to the amount of incident pulsed light reflected from the patient 9 is read out from the distance image sensor 38. The received light signal is converted into a digital signal by the AD converter 39. The digital signal is input to the control unit 26 through the interface circuit 40.

The distance image generation unit 53 of the control unit 26 generates the distance image data 23 on the basis of the digital signal input from the interface circuit 40 and outputs the distance image data 23 to the projection image generation unit 28 (Step S4). The process from Step S2 to Step S4 may be performed before the process in Step S or in parallel to the process in Step S1.

In addition, the position information acquisition unit 54 acquires the position of the leading end of the catheter 12 inserted into the body of the patient 9, using any one of the method using the transmission image data 22 and the method using the detection result of the amount of feed by the feed amount sensor 19, and outputs the leading end position information to the projection image generation unit 28 (Step S5). In a case in which the former method is used, it is possible to acquire the exact position of the leading end of the catheter 12 from the actually projected transmission image data 22. In a case in which the latter method is used, it is possible to simply acquire the position of the leading end of the catheter 12.

Then, as illustrated in FIG. 6, the projection image generation unit 28 recognizes the surface shape of the corresponding part of the patient 9 in which the leading end of the catheter 12 is located on the basis of the distance image data 23 input from the distance image generation unit 53 and the leading end position information input from the position information acquisition unit 54. Then, the projection image generation unit 28 transforms the transmission image data 22 to a shape fitted to the corresponding part of the patient 9 on the basis of the recognition result of the surface shape of the corresponding part to generate the projection image data 24 (Step S6).

In addition, the projection image generation unit 28 determines the display position and size of the projection image data 24 on the display optical element 42 such that the projection image based on the projection image data 24 is projected so as to overlap the corresponding part of the patient 9, on the basis of the distance to the corresponding part of the patient 9 which is determined from the distance image data 23 and the leading end position information and information about the focal length of the projection lens 46. Then, the projection image generation unit 28 outputs the projection image data 24 to the element driver 43.

At that time, as described with reference to FIG. 9, the generation of the projection image data 24 and the determination of the display position and size of the projection image data 24 by the projection image generation unit 28 may be performed such that the position of the leading end of the catheter 12 in the transmission image data 22 is aligned with the position of the leading end of the catheter 12 in the body of the patient 9. In this case, it is possible to accurately reproduce the position of the catheter 12 inserted into the body of the patient 9 on the projection image projected to the patient 9.

The element driver 43 displays the projection image data 24 input from the projection image generation unit 28 on the display optical element 42 in the size and at the position determined by the projection image generation unit 28. Then, the display optical element 42 modulates white light emitted from the LED light source 44 and image light of the projection image based on the projection image data 24 is projected to the corresponding part of the patient 9. As a result, as illustrated in FIG. 8, the projection image based on the projection image data 24 is projected onto the corresponding part of the patient 9. The position of the leading end of the catheter 12 in the body of the patient 9 is indicated by the projection image (Step S7).

Then, in a case in which the projection image is continuously projected, the process from Step S1 to Step S7 is repeatedly performed (Step S8). As a result, with the movement of the leading end of the catheter 12 in the blood vessel of the patient 9, the projection image data 24 is updated and the corresponding part of the patient 9 to which the projection image based on the projection image data 24 is projected is also changed.

Effect of First Embodiment

As described above, in the surgical support system 10 according to the first embodiment, the projection image data 24 corresponding to the surface shape of the corresponding part of the patient 9 is generated from the transmission image data 22 on the basis of the distance image data 23 of the patient 9 and the leading end position information indicating the position of the leading end of the catheter 12 in the body of the patient 9 and the image light of the projection image data 24 is projected to the corresponding part of the patient 9. Therefore, even in a case in which the patient 9 moves, it is possible to project the projection image indicating the position of the leading end of the catheter 12 in the body of the patient 9 to the corresponding part of the patient 9 in response to a change in the real-time position or posture of the patient. In addition, it is possible to reproduce the position of the catheter 12 inserted into the body of the patient 9 on the body surface of the patient 9.

Furthermore, the projection image data 24 is generated from the transmission image data 22 of the corresponding part of the patient 9 and the projection image based on the projection image data 24 is projected to the patient 9. Therefore, the doctor can insert the catheter 12 without averting the eyes from the patient 9 (without seeing a separate monitor).

Surgical Support System According to Second Embodiment

Next, a surgical support system (PM apparatus) according to a second embodiment will be described. The surgical support system 10 according to the first embodiment generates the projection image data 24 using the transmission image data 22. However, the surgical support system (PM apparatus) according to the second embodiment generates the projection image data 24 using the internal structure information 50 illustrated in FIG. 4.

The surgical support system according to the second embodiment basically has the same configuration as the surgical support system 10 according to the first embodiment except that it includes a PM apparatus 60 (see FIG. 11) different from the PM apparatus according to the first embodiment. Therefore, the components having the same functions or configurations as those in the first embodiment are denoted by the same reference numerals and the description thereof will not be repeated. In addition, in the surgical support system according to the second embodiment, the configuration related to the acquisition of the transmission image data 22 is not essential.

Figure 11:
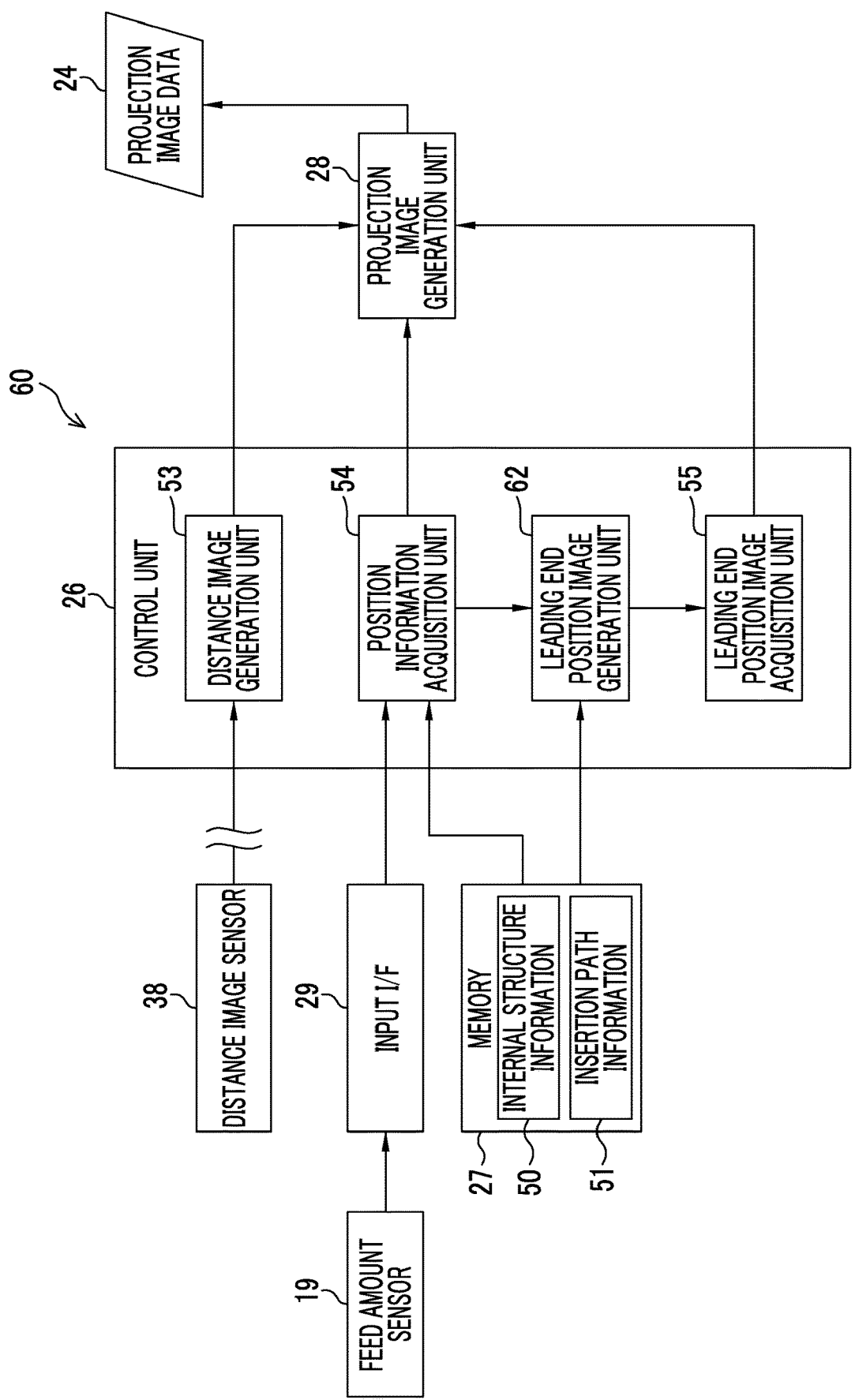
FIG. 11 is a block diagram illustrating the configuration of a projection mapping apparatus according to a second embodiment.

FIG. 11 is a block diagram illustrating the configuration of the PM apparatus 60 according to the second embodiment. As illustrated in FIG. 11, the PM apparatus 60 according to the second embodiment basically has the same configuration as the PM apparatus 20 according to the first embodiment except that the control unit 26 functions as a leading end position image generation unit 62 in addition to the distance image generation unit 53, the position information acquisition unit 54, and the leading end position image acquisition unit 55.

In a case in which the position information acquisition unit 54 according to the second embodiment acquires the position of the leading end of the catheter 12 inserted into the body of the patient 9 with the method using the transmission image data 22, the position information acquisition unit 54 receives the input of the transmission image data 22, similarly to the first embodiment.

The leading end position image generation unit 62 generates leading end position image data 64 (see FIG. 12) which is a leading end position image according to the invention indicating the position of the leading end of the catheter 12 in the body of the patient 9, on the basis of the leading end position information acquired from the position information acquisition unit 54 and the internal structure information 50 stored in the memory 27.

Figure 12:
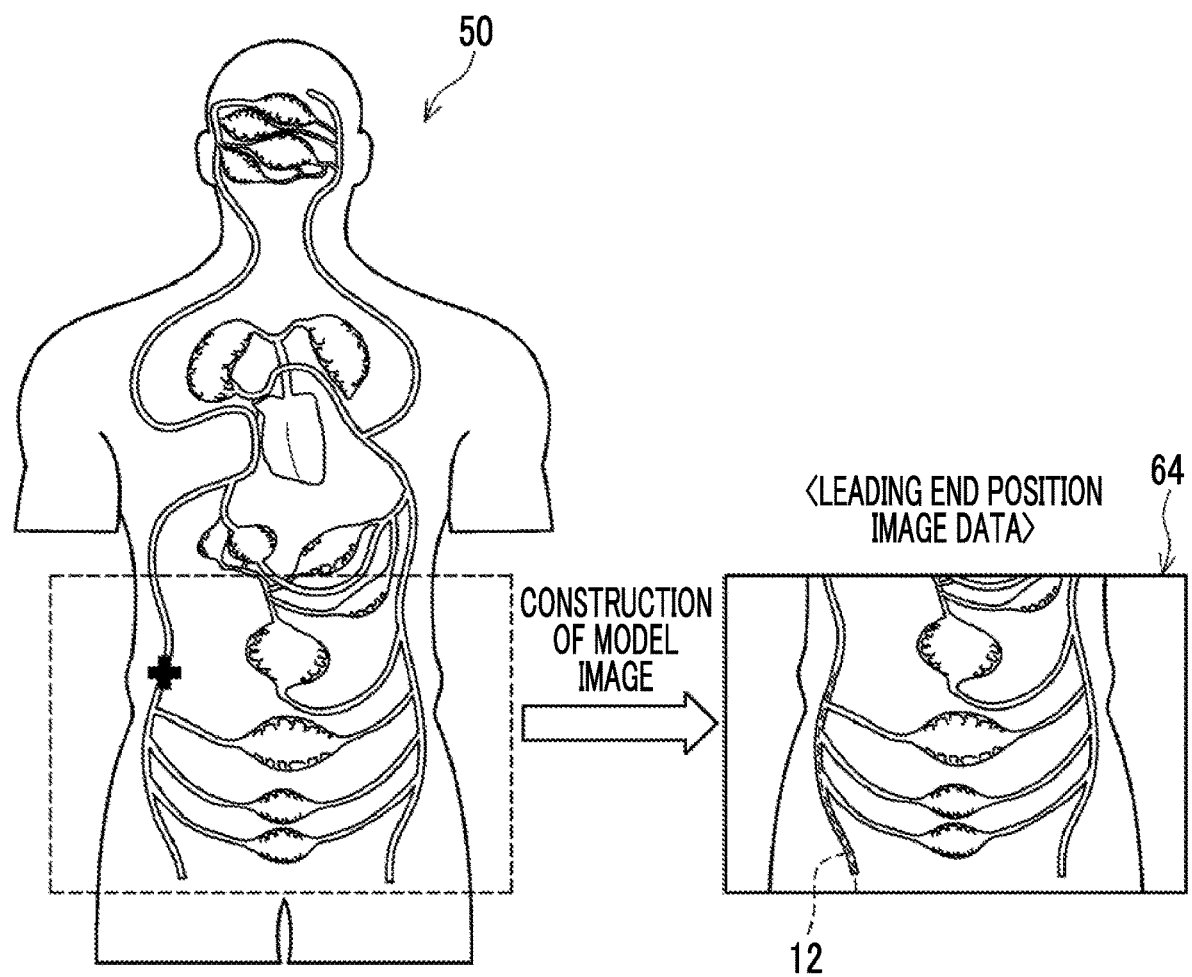
FIG. 12 is a diagram illustrating an example of a leading end position image data generation process performed by a leading end position image generation unit.

FIG. 12 is a diagram illustrating an example of the process of generating the leading end position image data 64 by the leading end position image generation unit 62. As illustrated in FIG. 12, the leading end position image generation unit 62 extracts a blood vessel structure in the corresponding part (represented by a dotted frame in FIG. 12) of the patient 9 as the internal structure information 50 on the basis of the leading end position information (represented by a cross in FIG. 12) acquired from the position information acquisition unit 54, with reference to the internal structure information 50 stored in the memory 27. Then, the leading end position image generation unit 62 constructs a model image (virtual image), which is obtained by modeling the extracted blood vessel structure of the corresponding part of the patient 9 and the catheter 12 in the blood vessel indicated by the leading end position information, to generate the leading end position image data 64.

The leading end position image data 64 includes a model image of the leading end of the catheter 12 and a model image of the blood vessels in the vicinity of the position of the leading end of the catheter 12. Therefore, the leading end position image data 64 indicates the position of the leading end of the catheter 12 in the body of the patient 9.

Returning to FIG. 11, the leading end position image acquisition unit 55 according to the second embodiment acquires the leading end position image data 64 from the leading end position image generation unit 62 and outputs the leading end position image data 64 to the projection image generation unit 28.

The projection image generation unit 28 according to the second embodiment generates the projection image data 24 from the leading end position image data 64 input from the leading end position image acquisition unit 55, on the basis of the distance image data 23 and the leading end position information. A detailed method for generating the projection image data 24 is basically the same as that in the first embodiment illustrated in FIG. 6. Since the configuration in which the subsequent processes are performed is the same as that in the first embodiment, the description thereof will not be repeated.

Operation of Surgical Support System According to Second Embodiment

Figure 13:
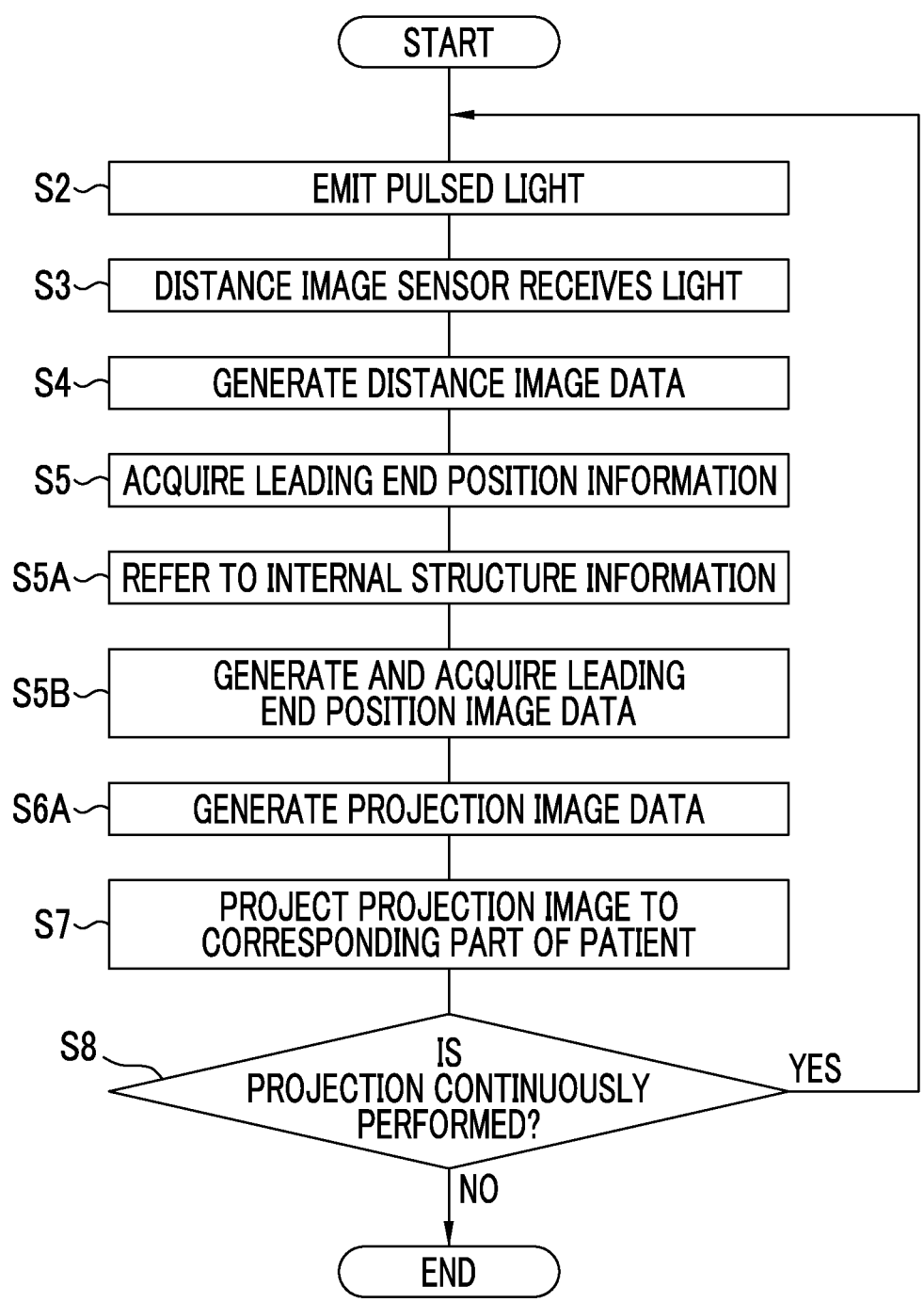
FIG. 13 is a flowchart illustrating the flow of a projection image projection process performed by the projection mapping apparatus of a surgical support system according to the second embodiment.

Next, the operation of the surgical support system according to the second embodiment will be described with reference to FIG. 13. FIG. 13 is a flowchart illustrating the flow of a projection image projection process performed by the PM apparatus 60 of the surgical support system according to the second embodiment. In the second embodiment, the process from Step S2 to Step S5 is the same as that in the first embodiment except that the transmission image data 22 (see FIG. 5) for generating the projection image data 24 in the first embodiment illustrated in FIG. 10 is not acquired.

After the process in Step S5, the leading end position image generation unit 62 extracts the blood vessel structure of the corresponding part of the patient 9 from the internal structure information 50 on the basis of the leading end position information acquired from the position information acquisition unit 54, with reference to the internal structure information 50 stored in the memory 27 (Step S5A). Then, as illustrated in FIG. 12, the leading end position image generation unit 62 constructs model images obtained by modeling the extracted blood vessel structure of the corresponding part of the patient 9 and the catheter 12 in the blood vessel indicated by the leading end position information to generate the leading end position image data 64 (Step S5B). In this way, it is possible to acquire the leading end position image data 64 indicating the position of the leading end of the catheter 12, without using the configuration for acquiring the transmission image data 22 according to the first embodiment.

In a case in which the leading end position image generation unit 62 generates the leading end position image data 64, the leading end position image acquisition unit 55 acquires the leading end position image data 64 from the leading end position image generation unit 62 and outputs the leading end position image data 64 to the projection image generation unit 28.

The projection image generation unit 28 generates the projection image data 24 from the leading end position image data 64 input from the leading end position image acquisition unit 55 on the basis of the distance image data 23 and the leading end position information, using basically the same method as that in the first embodiment (Step S6A).

Since the subsequent processes are the same as those in the first embodiment illustrated in FIG. 10, the detailed description thereof will not be repeated.

Effect of Second Embodiment

As described above, in the surgical support system according to the second embodiment, the projection image data 24 corresponding to the surface shape of the corresponding part of the patient 9 is generated from the leading end position image data 64 on the basis of the distance image data 23 of the patient 9 and the leading end position information indicating the position of the leading end of the catheter 12 in the body of the patient 9 and the image light of the projection image data 24 is projected to the corresponding part of the patient 9. Therefore, the same effect as that in the first embodiment is obtained.

Surgical Support System According to Third Embodiment

Next, a surgical support system according to a third embodiment will be described. In each of the above-described embodiments, the catheter 12 that passes through a known path (for example, blood vessels) in the body is given as an example of the medical instrument inserted into the body of the patient 9. However, in the surgical support system according to the third embodiment, a case in which a laparoscope 65 (corresponding to a medical instrument according to the invention (see FIG. 14)) is used will be described.

Figure 14:
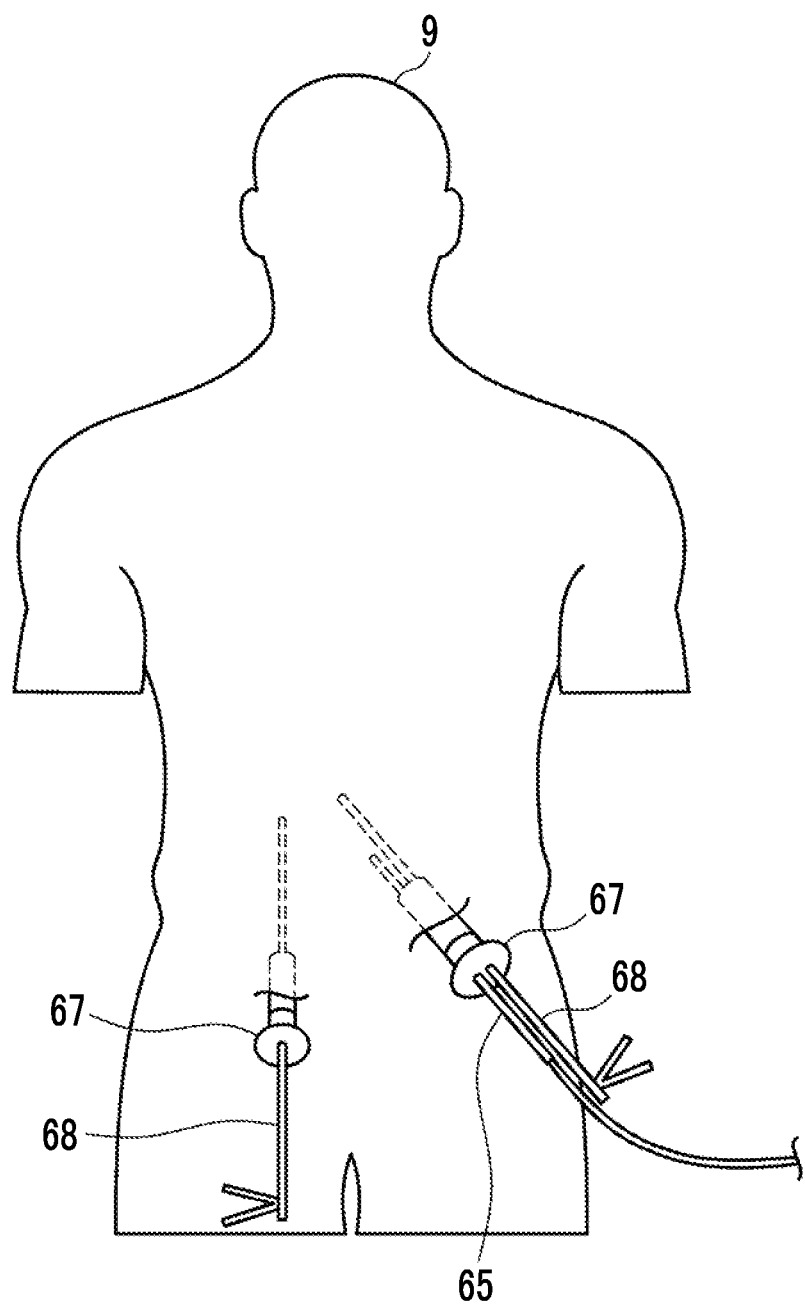
FIG. 14 is a diagram illustrating an example of laparoscopic surgery using a laparoscope.

FIG. 14 is a diagram illustrating an example of laparoscopic surgery using the laparoscope 65. As illustrated in FIG. 14, in the laparoscopic surgery, in a state in which a trocar 67 is inserted and fixed to a treatment hole formed in the body wall of the patient 9, the doctor inserts the laparoscope 65 into the body of the patient 9 (into a body cavity in the third embodiment) through an insertion hole of the trocar 67 and takes the image of the organs in the body using the laparoscope 65. Then, the doctor inserts a treatment tool 68, such as a forceps, into the body of the patient 9 through the insertion hole of the trocar 67 while seeing the captured image of the organs obtained by the laparoscope 65 and performs various treatments for the organs using the treatment tool 68.

In the surgical support system according to the third embodiment, a projection image indicating the position of the leading end of the laparoscope 65 in the body of the patient 9 is projected to the corresponding part of the patient according to the real-time position or posture of the patient 9. In addition, a projection image indicating the position of the leading end of the treatment tool 68 instead of the laparoscope 65 or at the same time as the laparoscope 65 may be projected to the corresponding part of the patient 9. In this example, a projection image indicating only the position of the leading end of the laparoscope 65 is projected to the corresponding part of the patient 9 for simplicity of description and the illustration of the drawings.

The surgical support system according to the third embodiment basically has the same configuration as the surgical support system according to the second embodiment among the embodiments except that it includes a PM apparatus 70 (see FIG. 15) different from the PM apparatuses according to the above-described embodiments and does not include the feed amount sensor 19. Therefore, components having the same functions or configurations as those in the second embodiment are denoted by the same reference numerals and the description thereof will not be repeated.

Figure 15:
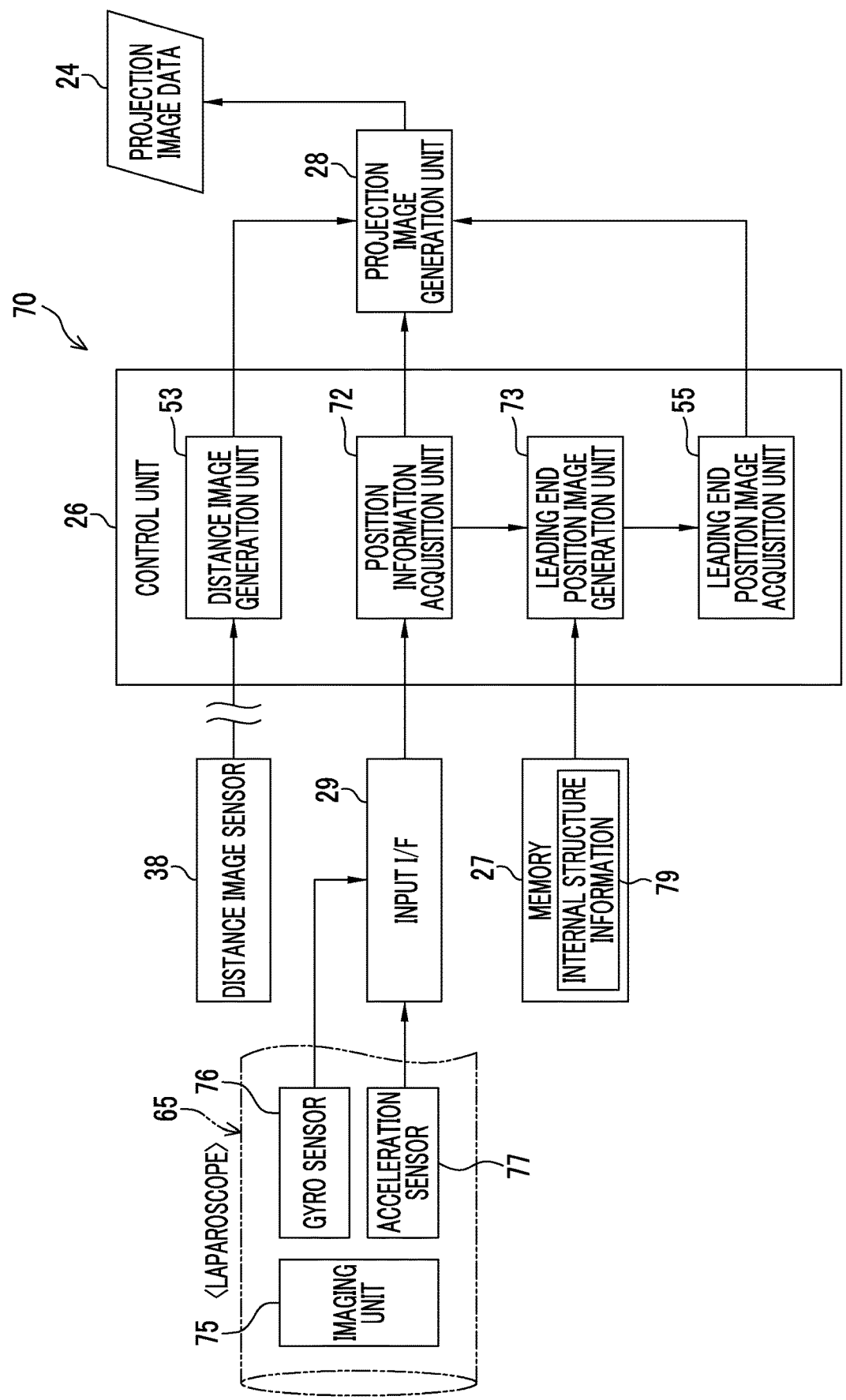
FIG. 15 is a block diagram illustrating the configuration of a projection mapping apparatus according to a third embodiment.

FIG. 15 is a block diagram illustrating the configuration of the PM apparatus 70 according to the third embodiment. As illustrated in FIG. 15, the PM apparatus 70 according to the third embodiment basically has the same configuration as the PM apparatus 60 according to the second embodiment except that the control unit 26 functions as a position information acquisition unit 72 and a leading end position image generation unit 73, in addition to the distance image generation unit 53 and the leading end position image acquisition unit 55.

The position information acquisition unit 72 acquires the position of the leading end of the laparoscope 65 inserted into the body of the patient 9. An imaging unit 75 including an imaging lens and various image sensors, a gyro sensor 76, and an acceleration sensor 77 are provided in a leading end portion of the laparoscope 65. The gyro sensor 76 measures acceleration that occurs in a case in which the leading end of the laparoscope 65 is rotated and outputs a measurement signal to the input I/F 29. The acceleration sensor 77 measures the acceleration (for example, acceleration along three axes, that is, the X-axis, the Y-axis, and the Z-axis) of the leading end of the laparoscope 65 and outputs the measurement signal to the input I/F 29.

The position information acquisition unit 72 acquires the measurement signals from the gyro sensor 76 and the acceleration sensor 77 through the input I/F 29 at a constant time interval. In addition, the position information acquisition unit 72 acquires the insertion position PS (see FIG. 16) of the laparoscope 65 into the body of the patient 9. A portion of the laparoscope 65 is outside the body of the patient 9 at the insertion position PS. Therefore, the position information acquisition unit 72 can acquire the insertion position PS of the laparoscope 65 on the basis of the recognition result obtained by analyzing, for example, the distance image data 23 to recognize the laparoscope 65 (trocar 67) outside the body of the patient 9. In addition, in a case in which the insertion position PS of the laparoscope 65 is predetermined, for example, space coordinates indicating the insertion position PS in internal structure information 79 (see FIG. 17), which will be described below, may be input to the PM apparatus 70.

Figure 16:
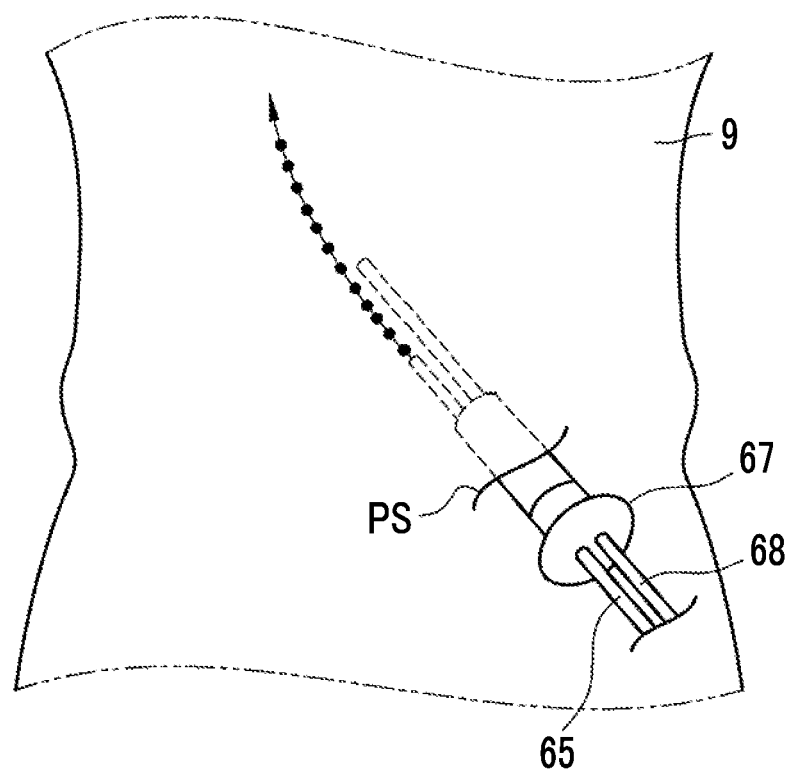
FIG. 16 is a diagram illustrating a process of acquiring the position of a leading end of the laparoscope in the body of the patient by a position information acquisition unit according to the third embodiment.

FIG. 16 is a diagram illustrating the process of acquiring the position of the leading end of the laparoscope 65 in the body of the patient 9 by the position information acquisition unit 72 according to the third embodiment. As illustrated in FIG. 16, the position information acquisition unit 72 detects the moving direction and the amount of movement of the leading end of the laparoscope 65 (the direction in which the leading end of the laparoscope 65 is moved and the distance that the leading end of the laparoscope 65 is moved) from the insertion position PS of the laparoscope 65 into the body of the patient 9, on the basis of the measurement signals input from the gyro sensor 76 and the acceleration sensor 77 through the input I/F 29 at a constant time interval. In this way, the position information acquisition unit 72 can acquire the position of the leading end of the laparoscope 65 inserted into the body of the patient 9. The position information acquisition unit 72 outputs leading end position information indicating the position of the leading end to the leading end position image generation unit 73 and the projection image generation unit 28.

Returning to FIG. 15, the leading end position image generation unit 73 generates leading end position image data 81 (see FIG. 18) which is leading end position image according to the invention indicating the position of the leading end of the laparoscope 65 in the body of the patient 9, on the basis of the leading end position information acquired from the position information acquisition unit 72 and the internal structure information 79 stored in the memory 27.

Figure 17:
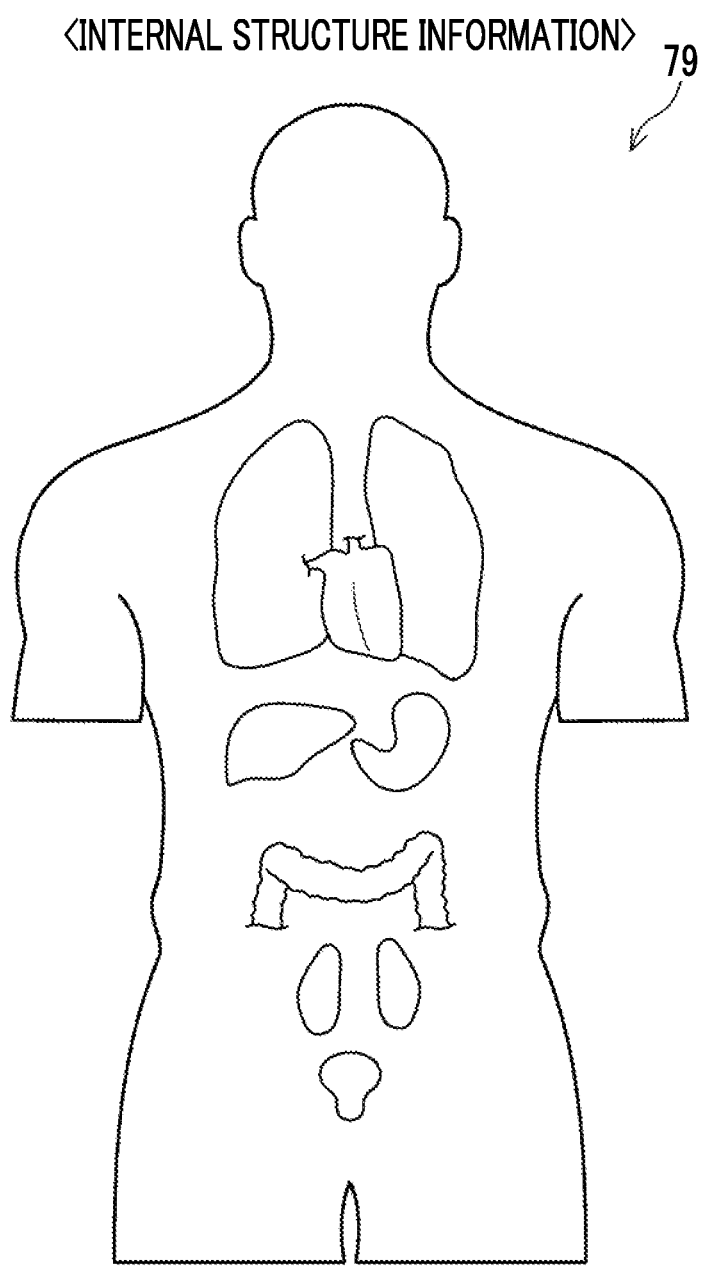
FIG. 17 is a diagram illustrating an example of internal structure information according to the third embodiment.

FIG. 17 is a diagram illustrating an example of the internal structure information 79 according to the third embodiment. As illustrated in FIG. 17, the internal structure information 79 in a case in which the laparoscope 65 is inserted into the body of the patient 9 is information indicating the arrangement structure of the organs (for example, the lung, the heart, the liver, the pancreas, and the kidney) in the body of the patient 9. The internal structure information 79 can be acquired by performing MRI or CT for the patient 9 in advance, similarly to the internal structure information 50 (see FIG. 4) described in the first embodiment. The arrangement structure of the organs in the body of the patient 9 is obtained with reference to the internal structure information 79.

Figure 18:
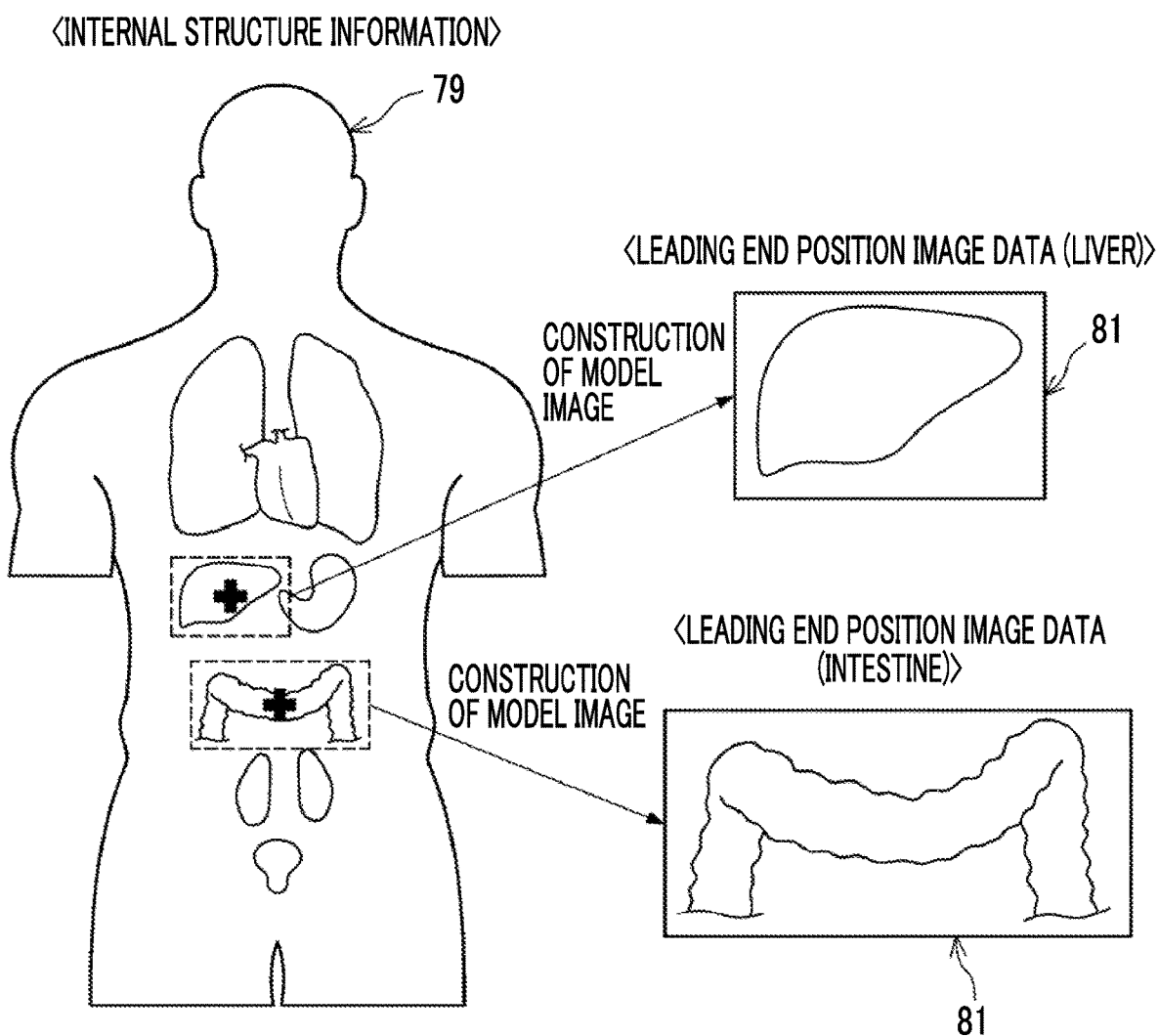
FIG. 18 is a diagram illustrating a leading end position image data generation process performed by a leading end position image generation unit according to the third embodiment.

FIG. 18 is a diagram illustrating the process of generating the leading end position image data 81 by the leading end position image generation unit 73 according to the third embodiment. As illustrated in FIG. 18, the leading end position image generation unit 73 recognizes the kind of organ in the corresponding part (represented by a dotted frame in FIG. 18) of the patient 9 on the basis of the leading end position information (represented by a cross in FIG. 18) acquired from the position information acquisition unit 72, with reference to the internal structure information 79 stored in the memory 27. The "corresponding part" of the patient 9 in the third embodiment is a part in which the leading end of the laparoscope 65 is located in the body of the patient 9. FIG. 18 illustrates a case in which the leading end is located at the "liver" and the "intestine".

Then, the leading end position image generation unit 73 constructs a model image (virtual image) obtained by modeling the organs in the corresponding part on the basis of the recognition result of the kind of organ in the corresponding part of the patient 9 to generate the leading end position image data 81. The leading end position image data 81 is the model image of the organs in the body of the patient 9 in which the leading end of the laparoscope 65 is located. Therefore, the leading end position image data 81 is an image indicating the position of the leading end of the laparoscope 65 in the body of the patient 9. In addition, the model image of the laparoscope 65 in the body of the patient 9 may be generated on the basis of the leading end position information acquired from the position information acquisition unit 72, the model image may be combined with the leading end position image data 81, and a composite image may be displayed.

Returning to FIG. 15, the leading end position image acquisition unit 55 according to the third embodiment basically has the same configuration as that in the second embodiment. The leading end position image acquisition unit 55 acquires the leading end position image data 81 from the leading end position image generation unit 73 and outputs the leading end position image data 81 to the projection image generation unit 28.

As described with reference to FIG. 6 in the first embodiment, the projection image generation unit 28 according to the third embodiment generates the projection image data 24 (see FIG. 19 and FIG. 20) corresponding to the surface shape of the corresponding part of the patient 9 from the leading end position image data 81 acquired from the leading end position image acquisition unit 55, on the basis of the distance image data 23 and the leading end position information.

In addition, similarly to the first embodiment, the projection image generation unit 28 according to the third embodiment determines the display position and size of the projection image data 24 on the display optical element 42 such that the projection image based on the projection image data 24 is projected so as to overlap the corresponding part of the patient 9. Then, the projection image generation unit 28 outputs the projection image data 24 to the element driver 43.

In a case in which the model image of the laparoscope 65 is combined with the leading end position image data 81, the generation of the projection image data 24 and the determination of the display position and size of the projection image data 24 on the display optical element 42 by the projection image generation unit 28 may be performed such that the position of the leading end of the laparoscope 65 in the projection image is aligned with the actual position of the leading end of the laparoscope 65 in the body of the patient 9, as described with reference to FIG. 9 in the first embodiment.

Figure 19:
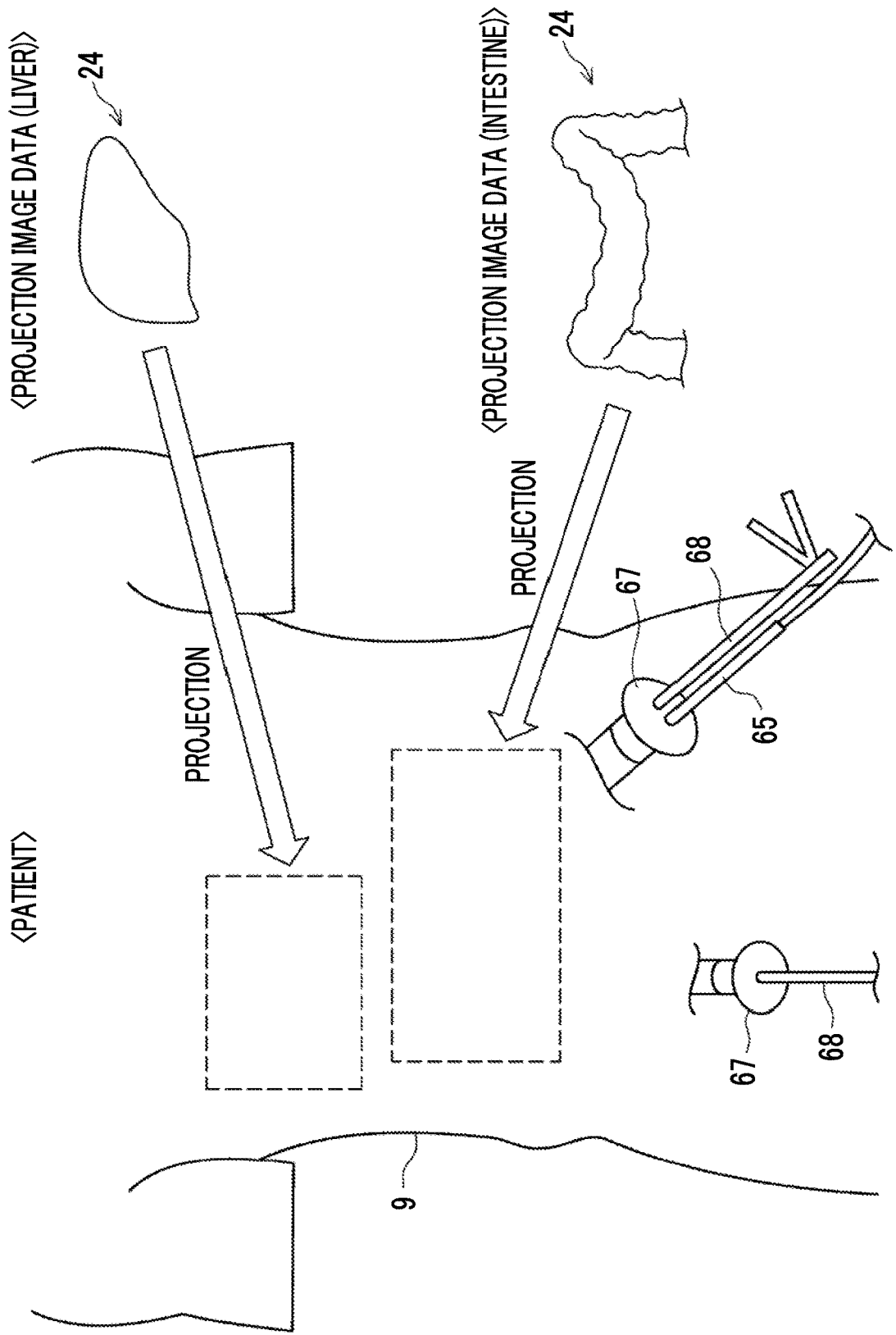
FIG. 19 is a diagram illustrating the projection of a projection image based on projection image data to the patient in the third embodiment.
Figures 20A, 20B:
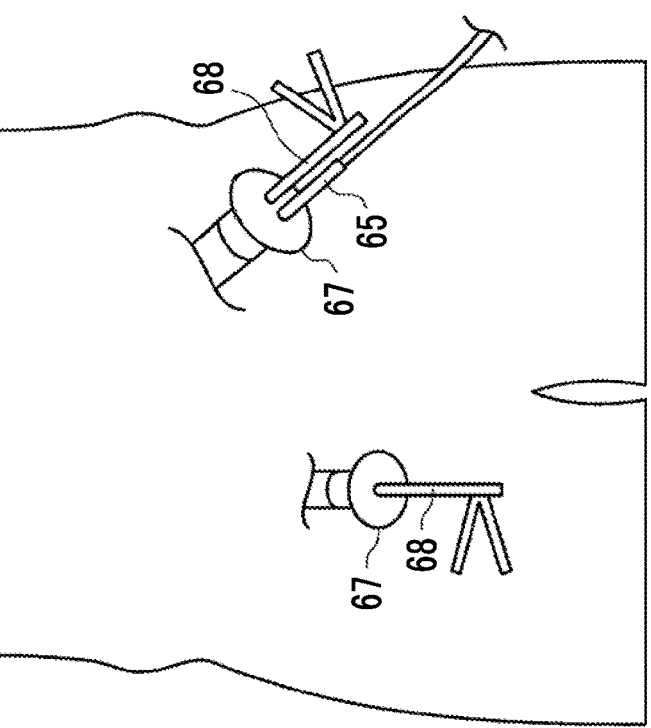
FIGS. 20A and 20B are a diagram illustrating a state in which the projection image based on the projection image data is projected to the patient in the third embodiment.

FIG. 19 is a diagram illustrating the projection of the projection image based on the projection image data 24 according to the third embodiment to the patient 9. FIGS. 20(A) and 20(B) are diagrams illustrating a state in which the projection image based on the projection image data 24 according to the third embodiment is projected to the patient 9. Here, FIG. 20(A) illustrates a case in which the leading end of the laparoscope 65 is located at the "intestine" and FIG. 20(B) illustrates a case in which the leading end of the laparoscope 65 is located at the "liver".

In a case in which the display optical element 42 displays the projection image data 24 as illustrated in FIG. 19, the display optical element 42 modulates white light emitted from the LED light source 44 and the image light of the projection image based on the projection image data 24 is projected to the corresponding part (represented by a dotted frame in FIG. 19) of the patient 9. Then, as illustrated in FIGS. 20(A) and 20(B), the projection image based on the projection image data 24 is projected onto the corresponding part of the patient 9. The position of the leading end of the laparoscope 65 in the body of the patient 9 is indicated by the projection image.

The generation of the distance image data 23 by the distance image generation unit 53, the acquisition of the leading end position information by the position information acquisition unit 72, the generation of the leading end position image data 81 by the leading end position image generation unit 73, and the acquisition of the leading end position image data 81 by the leading end position image acquisition unit 55 are repeatedly performed. With the repetition of the processes, the generation of new projection image data 24 by the projection image generation unit 28 is also repeatedly performed. As a result, the projection image projected to the corresponding part of the patient 9 is updated. For example, in a case in which the position of the leading end of the laparoscope 65 is moved from the "intestine" to the "liver", the position of the projection image projected to the patient 9 is moved from a corresponding part corresponding to the "intestine" to a corresponding part corresponding to the "liver" and the projection image is also switched from the image of the "intestine" to the image of the "liver", as illustrated in FIGS. 20(A) and 20(B).

Operation of Surgical Support System According to Third Embodiment

The operation of the surgical support system according to the third embodiment, that is, the flow of the projection image projection process is basically the same as the flow illustrated in FIG. 13 in the second embodiment. However, in the process of Step S5 in the third embodiment, the position information acquisition unit 72 acquires the position of the leading end of the laparoscope 65 inserted into the body of the patient 9 on the basis of the measurement signals from the gyro sensor 76 and the acceleration sensor 77 of the laparoscope 65. In the process of Steps S5A and S5B in the third embodiment, the leading end position image generation unit 73 generates the leading end position image data 81 on the basis of the leading end position information acquired from the position information acquisition unit 72, with reference to the internal structure information 79 in the memory 27.

Effect of Third Embodiment

As described above, in the surgical support system according to the third embodiment, the projection image data 24 corresponding to the surface shape of the corresponding part of the patient 9 is generated from the leading end position image data 81 on the basis of the distance image data 23 of the patient 9 and the leading end position information indicating the position of the leading end of the laparoscope 65 in the body of the patient 9 and the image light of the projection image data 24 is projected to the corresponding part of the patient 9. Therefore, the same effects as those in each of the above-described embodiments are obtained.

In addition, the position of the leading end of the laparoscope 65 inserted into the body of the patient 9 is acquired on the basis of the measurement signals from the gyro sensor 76 and the acceleration sensor 77 of the laparoscope 65. Therefore, even in a case in which the position of the leading end of the laparoscope 65 is freely moved in the body of the patient 9 (in the body cavity), it is possible to acquire the position of the leading end of the laparoscope 65 inserted into the body of the patient 9.

Surgical Support System According to Fourth Embodiment

Next, a surgical support system according to a fourth embodiment will be described. The position information acquisition unit 72 of the PM apparatus 70 in the surgical support system according to the third embodiment acquires the position of the leading end of the laparoscope 65 inserted into the body of the patient 9, on the basis of the measurement signals from the gyro sensor 76 and the acceleration sensor 77 of the laparoscope 65. In contrast, in the fourth embodiment, the position of the leading end of the laparoscope 65 inserted into the body of the patient 9 is acquired using captured image data 83 (see FIGS. 21A and 21B) of the body of the patient 9 captured by the laparoscope 65.

Figure 21:
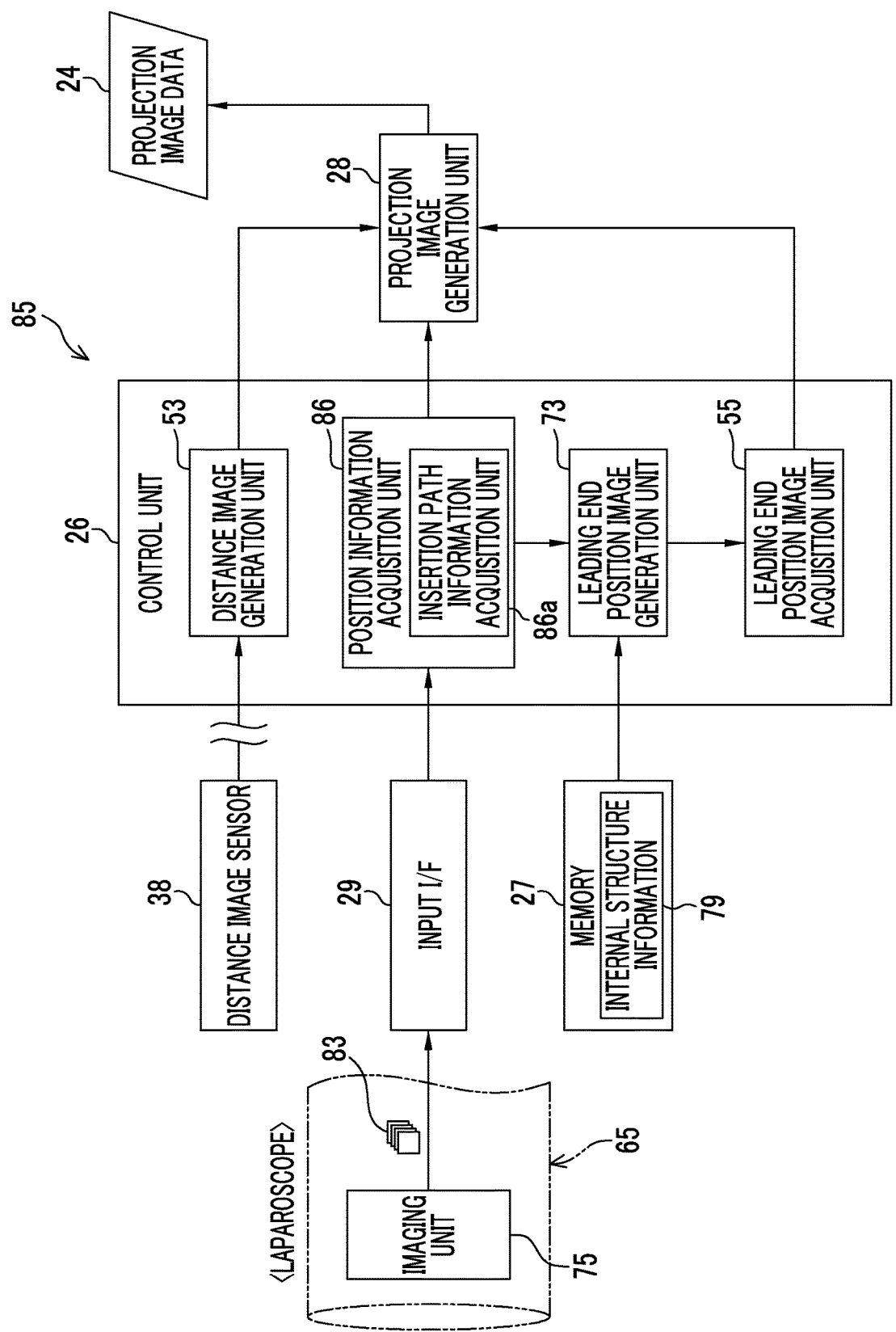
FIG. 21 is a block diagram illustrating the configuration of a projection mapping apparatus of a surgical support system according to a fourth embodiment.

FIGS. 21A and 21B are a block diagram illustrating the configuration of a PM apparatus 85 of the surgical support system according to the fourth embodiment. As illustrated in FIGS. 21A and 21B, the PM apparatus 85 according to the fourth embodiment basically has the same configuration as the PM apparatus 70 according to the third embodiment except that the control unit 26 functions as a position information acquisition unit 86 instead of the position information acquisition unit 72 according to the third embodiment. Therefore, components having the same functions or configurations as those in the third embodiment are denoted by the same reference numerals and the description thereof will not be repeated.

The position information acquisition unit 86 acquires the position of the leading end of the laparoscope 65 inserted into the body of the patient 9 (in the body cavity) using a method different from the method used by the position information acquisition unit 72 according to the third embodiment. The position information acquisition unit 86 acquires the captured image data 83 of the inside of the body of the patient 9 captured by the imaging unit 75 of the laparoscope 65 through the input I/F 29 at a constant time interval. In addition, the position information acquisition unit 86 acquires the insertion position PS (see FIG. 22) of the laparoscope 65 into the body of the patient 9, using the same method as the position information acquisition unit 72 according to the third embodiment.

Figure 22:
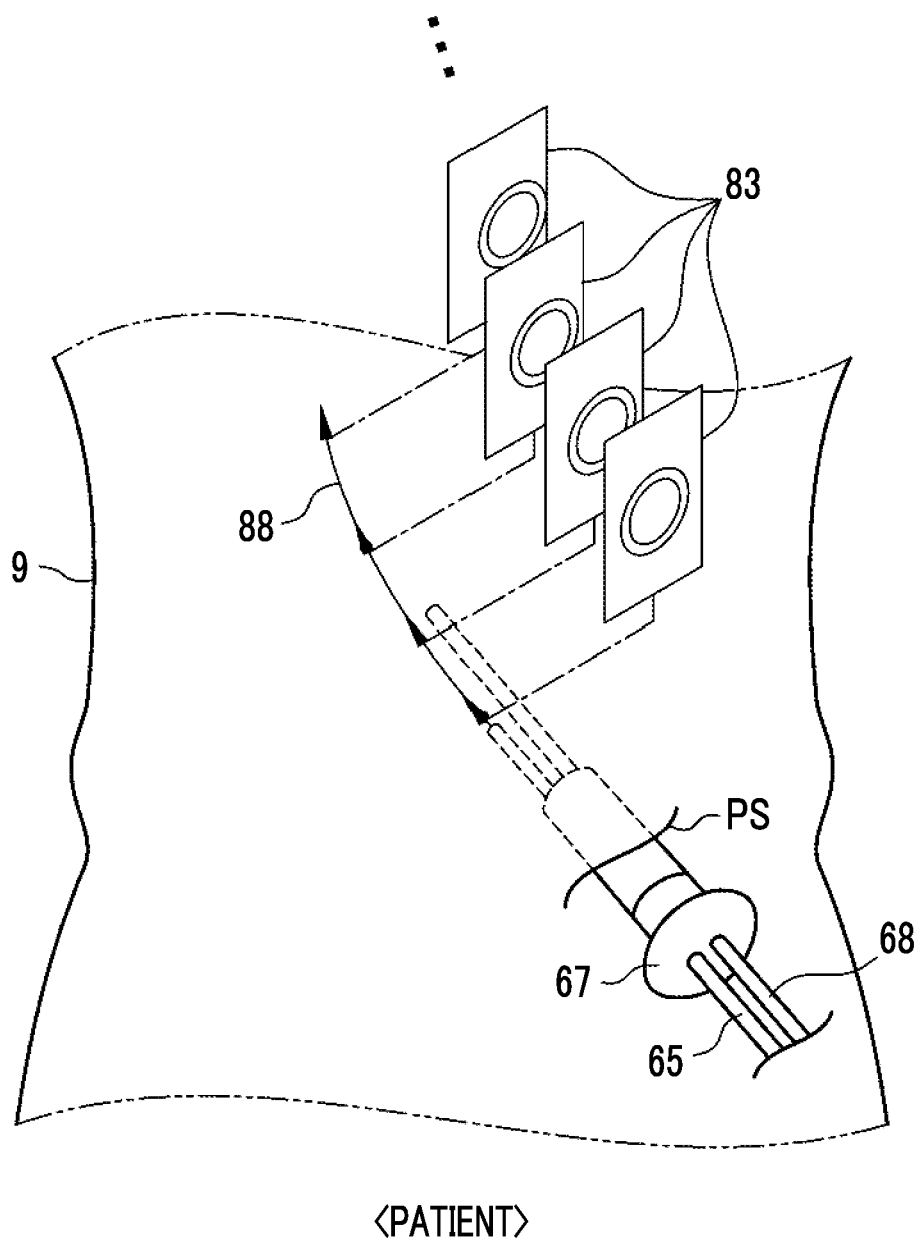
FIG. 22 is a diagram illustrating a process of acquiring the position of the leading end of the laparoscope in the body of the patient by a position information acquisition unit according to the fourth embodiment.

FIG. 22 is a diagram illustrating the process of acquiring the position of the leading end of the laparoscope 65 in the body of the patient 9 by the position information acquisition unit 86 according to the fourth embodiment. As illustrated in FIG. 22, the position information acquisition unit 86 acquires insertion path information 88 indicating the insertion path (movement path) of the leading end of the laparoscope 65 from the insertion position PS, on the basis of the continuous captured image data 83 input from the imaging unit 75 through the input I/F 29 at a constant time interval. That is, the position information acquisition unit 86 according to the fourth embodiment functions as an insertion path information acquisition unit 86a according to the invention.

Specifically, the insertion path information acquisition unit 86a performs a mapping process for the insertion path of the leading end of the laparoscope 65 from the insertion position PS, on the basis of the continuous captured image data 83 input from the imaging unit 75, using a known simultaneous localization and mapping (SLAM) technique. For example, the insertion path information acquisition unit 86a extracts each feature point (for example, corner points where image data are easily associated with each other) from the continuous captured image data 83 and calculates the trajectory of each feature point in the continuous captured image data 83 to perform the mapping process for the insertion path of the leading end of the laparoscope 65. In this way, insertion path information 88 indicating the insertion path of the leading end of the laparoscope 65 from the insertion position PS is acquired.

The insertion path information 88 indicates the moving direction and the amount of movement of the leading end of the laparoscope 65 from the insertion position PS (the direction in which the leading end of the laparoscope 65 is moved and the distance that the leading end of the laparoscope 65 is moved). Therefore, the position information acquisition unit 86 can acquire the position of the leading end of the laparoscope 65 inserted into the body of the patient 9, on the basis of the insertion path information 88 acquired by the insertion path information acquisition unit 86a. The position information acquisition unit 86 outputs the leading end position information indicating the position of the leading end to the leading end position image generation unit 73 and the projection image generation unit 28.

Since the configuration in which processes after the leading end position information is acquired are performed is basically the same as that in the PM apparatus 70 according to the third embodiment, the detailed description thereof will not be repeated.

Operation of Surgical Support System According to Fourth Embodiment

The operation of the surgical support system according to the fourth embodiment, that is, the flow of the projection image projection process is basically the same as the flow illustrated in FIG. 13 in the second embodiment as in the third embodiment. However, in the process of Step S5 in the fourth embodiment, the position information acquisition unit 86 acquires the position of the leading end of the laparoscope 65 inserted into the body of the patient 9, on the basis of the captured image data 83 captured by the imaging unit 75 of the laparoscope 65 and the insertion path information 88 acquired by the insertion path information acquisition unit 86a.

Effect of Fourth Embodiment

As described above, in the surgical support system according to the fourth embodiment, the projection image data 24 corresponding to the surface shape of the corresponding part of the patient 9 is generated from the leading end position image data 81 on the basis of the distance image data 23 of the patient 9 and the leading end position information indicating the position of the leading end of the laparoscope 65 in the body of the patient 9 and the image light of the projection image data 24 is projected to the corresponding part of the patient 9. Therefore, the same effects as those in each of the above-described embodiments are obtained.

In addition, the position of the leading end of the laparoscope 65 is acquired by calculating the insertion path information 88 indicating the insertion path of the leading end of the laparoscope 65 from the insertion position PS on the basis of the captured image data 83 continuously captured by the laparoscope 65. Therefore, even in a case in which the position of the leading end of the laparoscope 65 is freely moved in the body of the patient 9 (in the body cavity), it is possible to acquire the position of the leading end of the laparoscope 65 inserted into the body of the patient 9, similarly to the third embodiment.

Surgical Support System (PM Apparatus) According to Fifth Embodiment

Next, a surgical support system according to a fifth embodiment of the invention will be described. The PM apparatus of the surgical support system according to each of the above-described embodiments includes the LED light source 32 for acquiring the distance image data 23. In contrast, in the fifth embodiment, pulsed light is emitted to the patient 9 from an LED light source that emits pulsed light with the highest intensity (the largest amount of light) received by the distance image sensor 38 among a plurality of LED light sources which emit pulsed light components (measurement light components) with different wavelengths.

Figure 23:
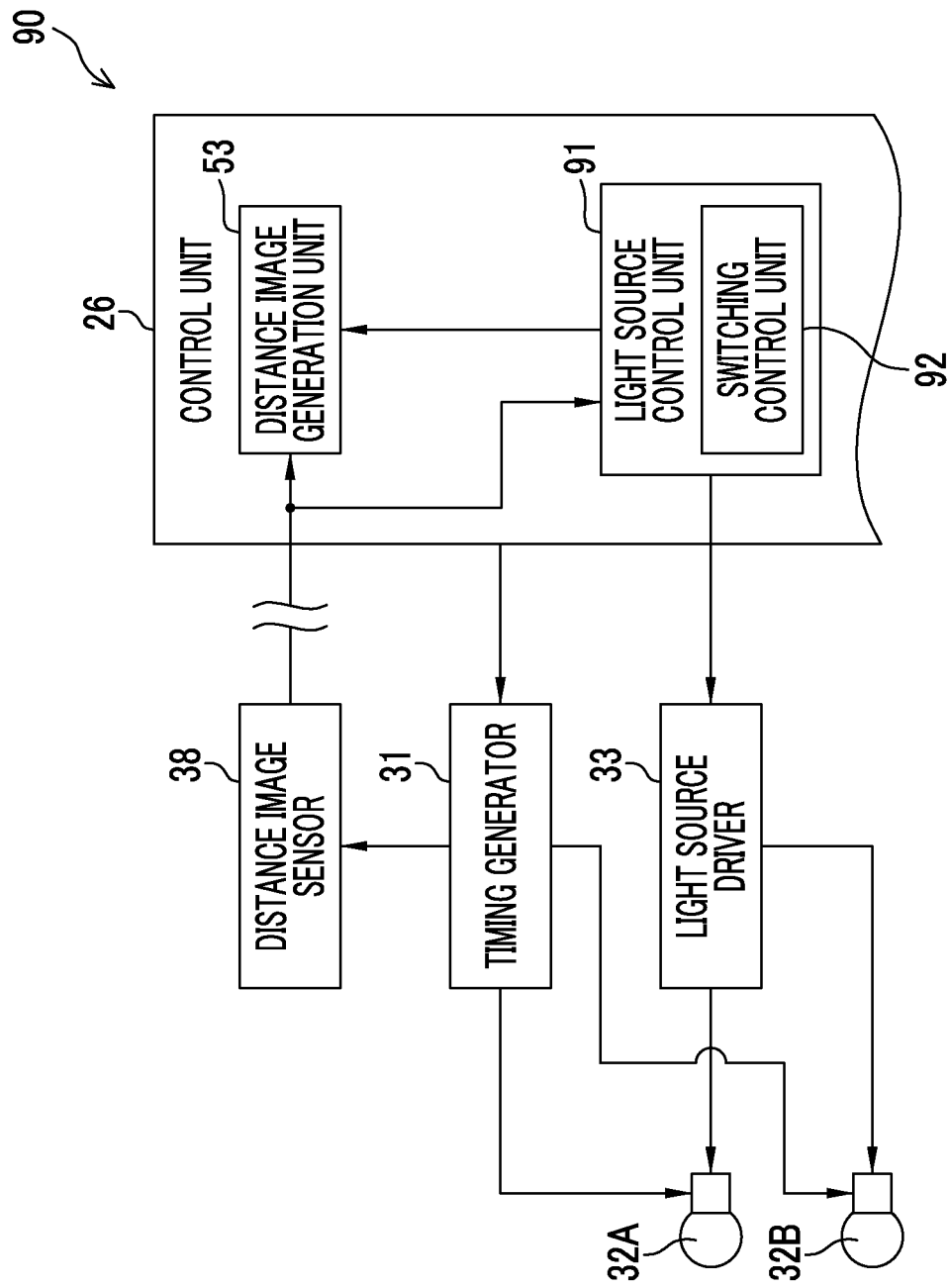
FIG. 23 is a block diagram illustrating the configuration of a projection mapping apparatus of a surgical support system according to a fifth embodiment.

FIG. 23 is a block diagram illustrating the configuration of a PM apparatus 90 in the surgical support system according to the fifth embodiment. As illustrated in FIG. 23, the PM apparatus 90 according to the fifth embodiment basically has the same configuration as the PM apparatus according to each of the above-described embodiments except that PM apparatus 90 includes LED light sources 32A and 32B (corresponding to light source units according to the invention) which emit pulsed light components with different wavelengths and the control unit 26 functions as a light source control unit 91 in addition to, for example, the distance image generation unit 53. Therefore, components having the same functions or configurations as those in each of the above-described embodiments are denoted by the same reference numerals and the description thereof will not be repeated.

The driving of the LED light sources 32A and 32B is controlled by the light source driver 33, similarly to the LED light source 32 according to each of the above-described embodiments. The LED light sources 32A and 32B emit pulsed light with a constant pulse width in synchronization with the timing signal input from the timing generator 31.

The light source control unit 91 controls the light source driver 33 such that the emission of the pulsed light from the LED light sources 32A and 32B is controlled. The light source control unit 91 also functions as a switching control unit 92.

The switching control unit 92 performs control such that the LED light sources 32A and 32B sequentially emit pulsed light before the distance image generation unit 53 generates the distance image data 23 (for example, in a case in which the PM apparatus 90 starts), thereby switching the LED light sources emitting the pulsed light to the patient 9. In this way, the wavelengths of the pulsed light components emitted from the PM apparatus 90 to the patient 9 are switched.

Since the wavelengths of the pulsed light components emitted to the patient 9 are switched as described above, the distance image sensor 38 according to the fifth embodiment receives the pulsed light with each wavelength reflected from the patient 9 through the focus lens 36. Here, the reflectance of the body surface (irradiation surface) of the patient 9 with respect to each wavelength of the pulsed light varies depending on, for example, the material or color of the clothes of the patient 9, the skin color of the patient 9, and the incident angle of the pulsed light on the patient 9. Therefore, the intensity of the pulsed light reflected from the patient 9 varies depending on the wavelength of the pulsed light.

The exposure time of the distance image sensor 38 according to the fifth embodiment is controlled by the timing signal input from the timing generator 31 in synchronization with the emission of the pulsed light from each of the LED light sources 32A and 32B. As described above, charge corresponding to the amount of pulsed light incident for an exposure period is accumulated in each light receiving element of the distance image sensor 38. Therefore, the amount of exposure of the distance image sensor 38 increases as the amount of pulsed light incident for the exposure period, that is, the intensity of pulsed light reflected from the patient 9 increases. A received light signal corresponding to the amount (intensity) of incident pulsed light reflected from the patient 9 is read out from the distance image sensor 38 for each wavelength of the pulsed light. The received light signal for each wavelength is converted into a digital signal by the AD converter 39. The digital signal is input to the light source control unit 91 through the interface circuit 40.

The light source control unit 91 compares the intensities of the pulsed light components with each wavelength received by the distance image sensor 38, on the basis of the digital signals for each wavelength of the pulsed light. Then, the light source control unit 91 determines whether an LED light source that emits pulsed light with a wavelength at which intensity is the highest among the pulsed light components with each wavelength received by the distance image sensor 38 is the LED light source 32A or the LED light source 32B. Then, the light source control unit 91 decides the LED light source that emits pulsed light with the wavelength at which intensity is the highest as the LED light source that emits pulsed light for generating the distance image data 23 and controls the light source driver 33 such that the decided LED light source emits pulsed light.

In a case in which the LED light source that emits pulsed light with the wavelength at which intensity is the highest irradiates the patient 9 with pulsed light under the control of the light source control unit 91, the distance image generation unit 53 according to the fifth embodiment generates the distance image data 23 on the basis of the digital signal input from the distance image sensor 38 through the AD converter 39 and the interface circuit 40.

Since the configuration in which processes after the distance image data 23 is generated are performed is basically the same as that in the PM apparatus according to each of the above-described embodiments, the detailed description thereof will not be repeated.

Operation of Surgical Support System According to Fifth Embodiment

Figure 24:
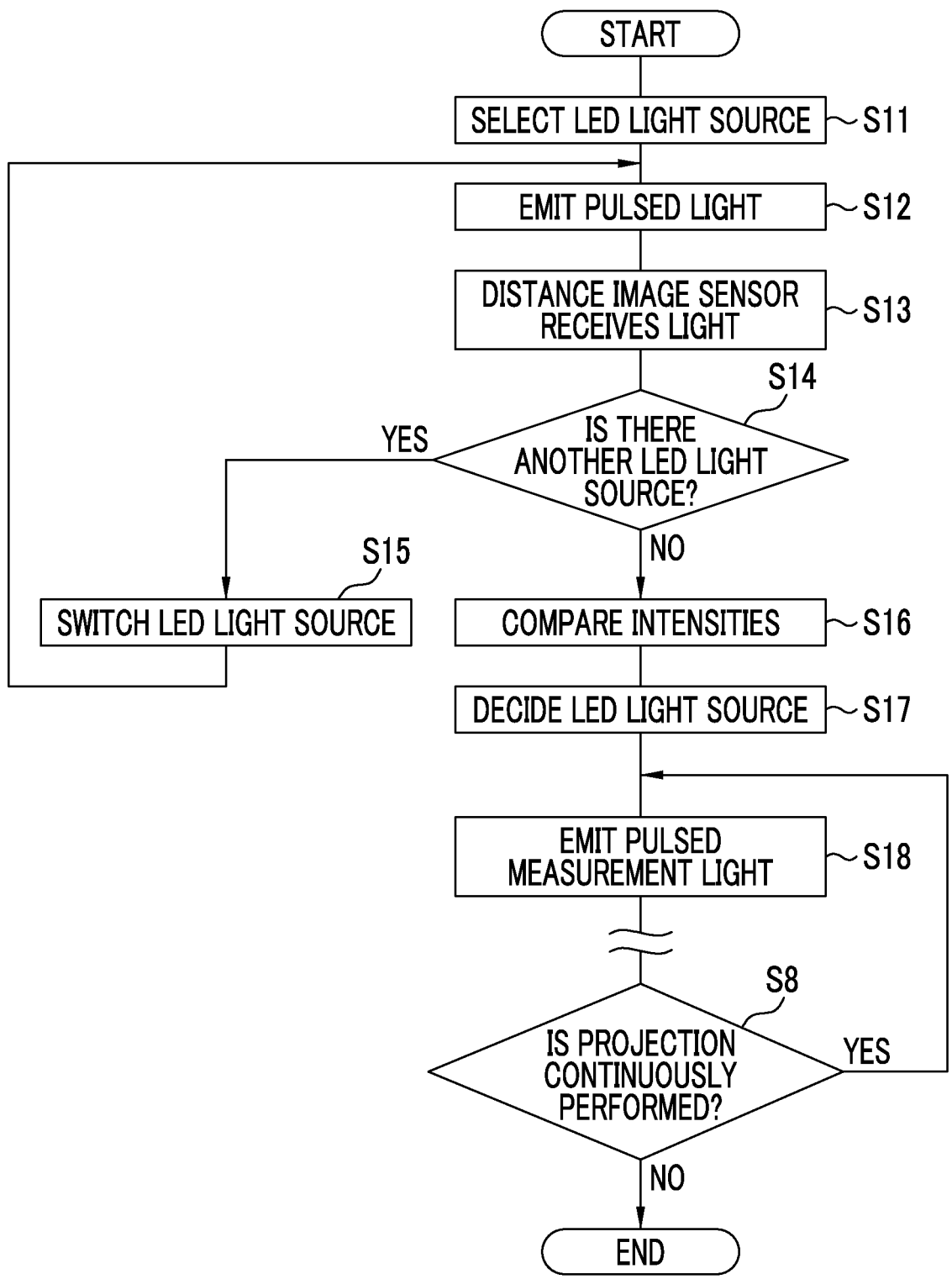
FIG. 24 is a flowchart illustrating the flow of a process of determining an LED light source that emits pulsed light for generating distance image data.

The operation of the surgical support system according to the fifth embodiment, that is, the flow of the process of determining an LED light source will be described with reference to FIG. 24. FIG. 24 is a flowchart illustrating the flow of the process of determining an LED light source that emits pulsed light for generating the distance image data 23.

In a case in which the PM apparatus 90 starts, the switching control unit 92 of the light source control unit 91 in the control unit 26 selects an LED light source that emits pulsed light first from the LED light sources 32A and 32B (Step S11). Here, it is assumed that the LED light source 32A is selected. Then, the light source control unit 91 controls the light source driver 33 such that the LED light source 32A starts to be driven. Then, the LED light source 32A emits pulsed light in synchronization with the timing signal input from the timing generator 31. Then, the pulsed light emitted from the LED light source 32A is emitted to the patient 9 by the projection lens 35 (Step S12).

The pulsed light emitted to the patient 9 is reflected from the body surface of the patient 9 and is incident on the focus lens 36. The pulsed light is focused on the distance image sensor 38 by the focus lens 36. Then, the pulsed light reflected from the patient 9 is received by the distance image sensor 38 (Step S13). Then, a received light signal corresponding to the amount of incident pulsed light reflected from the patient 9 is read out from the distance image sensor 38. The received light signal is converted into a digital signal by the AD converter 39. The digital signal is input to the light source control unit 91 through the interface circuit 40.

Then, the switching control unit 92 of the light source control unit 91 controls the light source driver 33 such that the driving of the LED light source 32A is stopped and the LED light source 32B starts to be driven. That is, the switching control unit 92 switches the LED light source that irradiates the patient 9 with pulsed light from the LED light source 32A to the LED light source 32B (YES in Step S14 and Step S15).

After the LED light source is switched to the LED light source 32B, the process in Steps S12 and S13 is repeatedly performed. Then, the LED light source 32B irradiates the patient 9 with pulsed light and a received light signal corresponding to the amount of incident pulsed light reflected from the patient 9 is read out from the distance image sensor 38. Then, the received light signal is converted into a digital signal by the AD converter 39. The digital signal is input to the light source control unit 91 through the interface circuit 40.

In this example, since the LED light sources 32A and 32B with different wavelengths are used, the light source control unit 91 compares the intensities of the pulsed light components with each wavelength received by the distance image sensor 38 on the basis of the digital signals for each wavelength of the pulsed light (NO in Step S14 and Step S16). Then, the light source control unit 91 determines an LED light source that emits pulsed light with a wavelength at which intensity is the highest among the pulsed light components with each wavelength received by the distance image sensor 38 and decides the LED light source as the LED light source that emits pulsed light for generating the distance image data 23 (Step S17). Then, the light source control unit 91 controls the light source driver 33 such that the decided LED light source emits pulsed light (Step S18).

The subsequent processes are basically the same as the processes after Step S3 illustrated in FIG. 10 or FIG. 13. Therefore, here, the detailed description thereof will not be repeated.

Effect of Fifth Embodiment

As described above, in the PM apparatus 90 of the surgical support system according to the fifth embodiment, pulsed light is emitted to the patient 9 by an LED light source that emits pulsed light with higher intensity (a larger amount of light) received by the distance image sensor 38 of the LED light sources 32A and 32B that emit pulsed light components with different wavelengths. Therefore, it is possible to improve the accuracy of determining the distance to the patient 9 based on the distance image data 23 or the accuracy of determining the shape of the patient 9.

Modification Examples of Fifth Embodiment

The PM apparatus 90 according to the fifth embodiment includes the LED light sources 32A and 32B that emit pulsed light components with different wavelengths. However, the PM apparatus 90 may include three or more LED light sources with different wavelengths. In this case, pulsed light is emitted to the patient 9, using an LED light source that emits pulsed light with the highest intensity received by the distance image sensor 38 among the LED light sources.

In the fifth embodiment, the LED light sources that emit pulsed light are switched. However, for example, a plurality of filters that transmit light components with different wavelengths may be selectively provided on the optical path of pulsed light emitted from the LED light source to switch the wavelengths of pulsed light emitted to the patient 9.

Surgical Support System (PM Apparatus) According to Sixth Embodiment

Next, a surgical support system according to a sixth embodiment of the invention will be described. In the PM apparatuses according to each of the above-described embodiments, the distance image generation unit 53 generates the distance image data 23 of the entire range (including almost the entire range) of the patient 9. However, in a PM apparatus 100 (see FIG. 25) of the surgical support system according to the sixth embodiment, the generation range AT of the distance image data 23 is set according to the projection range AP of the projection image projected to the patient 9 (see FIGS. 26A and 26B).

Figure 25:
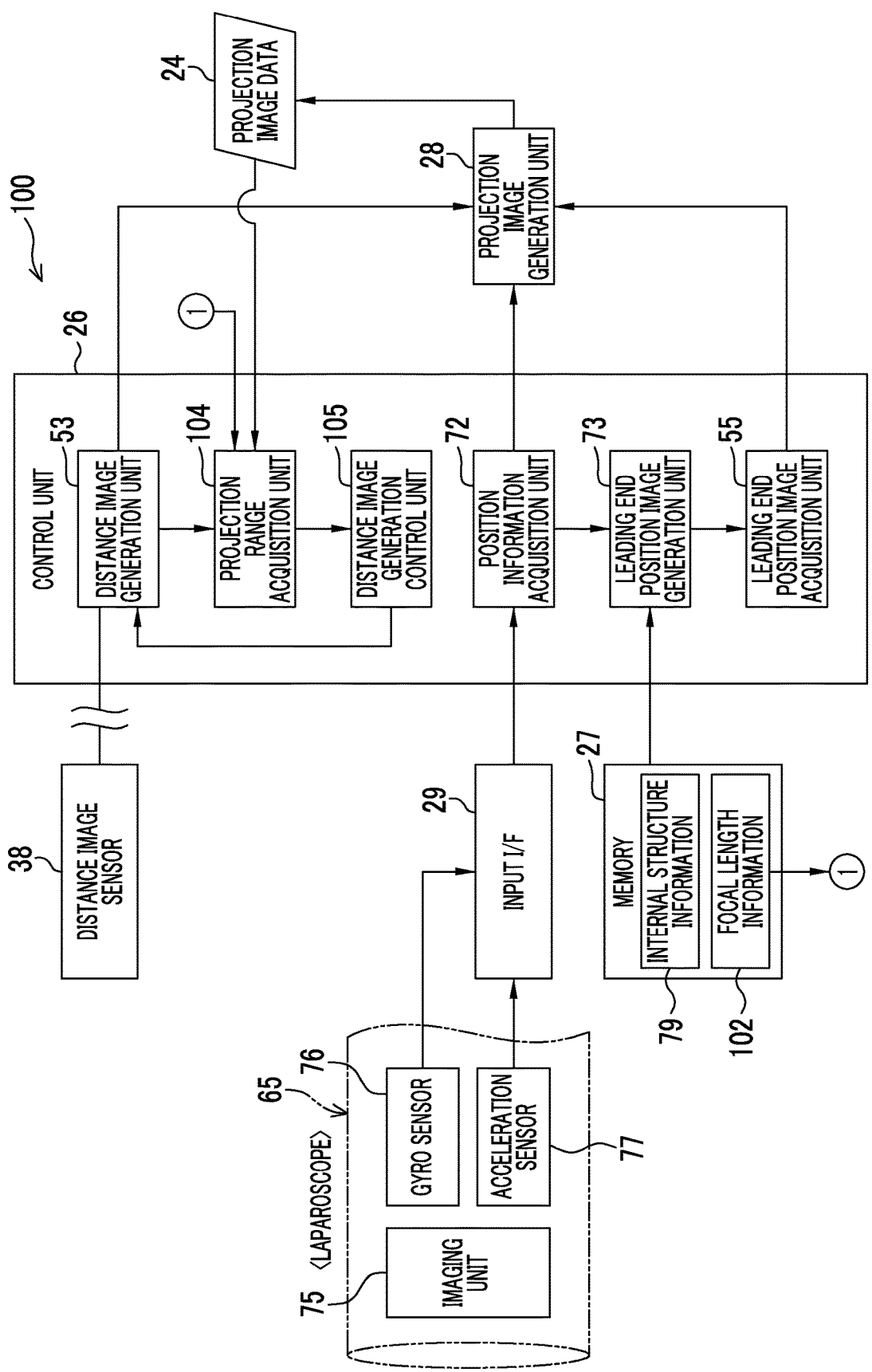
FIG. 25 is a block diagram illustrating the configuration of a projection mapping apparatus of a surgical support system according to a sixth embodiment.

FIG. 25 is a block diagram illustrating the configuration of the PM apparatus 100 of the surgical support system according to the sixth embodiment. As illustrated in FIG. 25, the PM apparatus 100 according to the sixth embodiment basically has the same configuration as the PM apparatus 70 according to the third embodiment except that focal length information 102 is stored in the memory 27 and the control unit 26 functions as a projection range acquisition unit 104 and a distance image generation control unit 105, in addition to, for example, the distance image generation unit 53. Therefore, components having the same functions or configurations as those in the third embodiment are denoted by the same reference numerals and the description thereof will not be repeated.

The focal length information 102 is information indicating the focal length of the projection lens 46 (see FIG. 2). In this example, since the distance between the PM apparatus 100 and the patient 9 is basically constant (including substantially constant), the focal length of the projection lens 46 is predetermined according to the distance between the PM apparatus 100 and the patient 9.

The projection range acquisition unit 104 acquires the projection range AP (see FIGS. 26A and 26B) of the projection image projected from the PM apparatus 100 to the patient 9, on the basis of the focal length information 102 read out from the memory 27, the distance to the patient 9 indicated by the distance image data 23 which has been previously generated by the distance image generation unit 53, and the projection image data 24 (including the display position and size of the projection image data 24 on the display optical element 42) generated by the projection image generation unit 28. Then, the projection range acquisition unit 104 outputs the acquired projection range AP to the distance image generation control unit 105.

The distance image generation control unit 105 controls the distance image generation unit 53 such that the generation range AT (see FIGS. 26A and 26B) in which the distance image data 23 is generated by the distance image generation unit 53 is set.

FIGS. 26(A) and 26(B) are diagrams illustrating the setting of the generation range AT of the distance image data 23 by the distance image generation control unit 105. As illustrated in FIGS. 26(A) and 26(B), the distance image generation control unit 105 sets the generation range AT of the distance image data 23 in correspondence with the projection range AP acquired by the projection range acquisition unit 104. The generation range AT is set so as to be larger than the projection range AP by a predetermined size. Then, the distance image generation control unit 105 outputs information related to the set generation range AT to the distance image generation unit 53.

The distance image generation unit 53 according to the sixth embodiment generates the distance image data 23 on the basis of a digital signal corresponding to the generation range AT among the digital signals which have been read out from the distance image sensor 38 and then input to the distance image generation unit 53 through, for example, the AD converter 39 and the interface circuit 40. This configuration makes it unnecessary to generate the distance image data 23 for the entire range of the patient 9. Therefore, it is possible to reduce the amount of calculation required for the process of generating the distance image data 23.

In a case in which the focus lens 36 (see FIG. 2) has a zoom function and the distance image data 23 is generated, the control unit 26 may control the lens driver 37 such that a zooming operation of changing the angle of view so as to be fitted to the generation range AT is performed. In this case, the distance image generation unit 53 generates the distance image data 23 on the basis of the digital signal which has been read out from the distance image sensor 38 and then input to the distance image generation unit 53 through, for example, the AD converter 39 and the interface circuit 40. This configuration makes it possible to increase the resolution of the distance image data 23 and to improve the accuracy of detecting the distance to the patient 9 or the accuracy of detecting the unevenness of the surface shape of the patient 9.

In a case in which the zooming operation is performed, the PM apparatus 100 may be provided with a pan/tilt mechanism and a pan/tilt control unit that drives the pan/tilt mechanism such that the PM apparatus 100 (focus lens 36) is oriented in the direction of the generation range AT, on the basis of the setting result of the generation range AT by the distance image generation control unit 105.

Since the PM apparatus 100 is basically the same as the PM apparatus 70 according to the third embodiment except the configuration related to the process of generating the distance image data 23, the detailed description thereof will not be repeated.

Effect of Sixth Embodiment

As described above, in the PM apparatus 100 of the surgical support system according to the sixth embodiment, the distance image generation unit 53 sets the generation range AT in which the distance image data 23 is generated, in correspondence with the projection range AP of the projection image projected to the patient 9. Therefore, it is unnecessary to generate the distance image data 23 for the entire range of the patient 9 and it is possible to reduce the amount of calculation required for the process of generating the distance image data 23.

In a case in which the distance image generation control unit 105 sets the generation range AT and the zooming operation of changing the angle of view so as to be fitted to the generation range AT is performed, it is possible to increase the resolution of the distance image data 23. Therefore, it is possible to improve the accuracy of detecting the distance to the patient 9 or the accuracy of detecting the unevenness of the surface shape of the patient 9.

Modification Examples of Sixth Embodiment

In the sixth embodiment, the configuration in which the generation range AT of the distance image data 23 is set according to the projection range AP of the projection image projected to the patient 9 is combined with the configuration according to the third embodiment. However, the configuration in which the generation range AT is set may be combined with other configurations according to each of the above-described embodiments.

Others

In the first embodiment, X-ray image data has been described as an example of the transmission image data 22. However, various transmission images of the corresponding part of the patient 9, such as MRI image data and CT image data, may be used.

In the first and second embodiments, the catheter 12 has been described as an example of the medical instrument that is inserted along a known path in the body of the patient 9. However, the invention can be applied to a case in which an upper gastrointestinal endoscope or a lower gastrointestinal endoscope is inserted into the body of the patient 9. In the third and subsequent embodiments, the laparoscope 65 has been described as an example of the medical instrument. However, the medical instrument is not particularly limited as long as it is inserted into the body of the patient 9.

In the PM apparatus according to each of the above-described embodiments, the distance image data 23 is acquired by a so-called time-of-flight (TOF) method which reads out the received light signal indicating distance information corresponding to the time of flight of the pulsed light which has been reflected from the patient 9 and then incident on the distance image sensor 38 from the distance image sensor 38 and generates the distance image data 23 on the basis of the read received light signal. However, the distance image data 23 may be acquired by a so-called pattern irradiation (projector-camera) method.

In each of the above-described embodiments, the projection image generation unit 28 is separately provided in the control unit 26. However, the control unit 26 may be configured so as to function as the projection image generation unit 28. In addition, in each of the above-described embodiments, the PM apparatus in which the distance image generation function and the projection image projection function are integrated has been described as an example. However, the distance image generation function and the projection function may be separated from each other.

In each of the above-described embodiments, a person (patient 9) has been described as an example of the subject. However, the invention can be applied to a case in which the medical instrument is inserted into various subjects such as animals other than the person.

EXPLANATION OF REFERENCES

10: surgical support system
12: catheter
18: transmission image generation unit
19: feed amount sensor
20, 60, 70, 85, 90, 100: projection mapping apparatus
22: transmission image data
23: distance image data
24: projection image data
26: control unit
28: projection image generation unit
32: LED light source
35: projection lens
36: focus lens
38: distance image sensor
42: display optical element
44: LED light source
46: projection lens
50, 79: internal structure information
51: insertion path information
53: distance image generation unit
54, 72, 86: position information acquisition unit
55: leading end position image acquisition unit
62, 73: leading end position image generation unit
64, 81: leading end position image data
65: laparoscope
75: imaging unit
76: gyro sensor
77: acceleration sensor
83: captured image data
91: light source control unit
92: switching control unit
104: projection range acquisition unit
105: distance image generation control unit

What is claimed is:

1. A projection mapping apparatus comprising:
a light source that emits measurement light to irradiate a subject with the measurement light;
a distance image sensor in which a plurality of light receiving elements are two-dimensionally arranged, wherein an amount of measurement light received by each light receiving element of the plurality of light receiving elements two-dimensionally arranged in the distance image sensor is dependent on a distance between each light receiving element and a surface of the subject, the distance image sensor outputting the amount of measurement light received by each element as a received light signal to a processor, the processor configured to:
acquire the received light signal outputted by the distance image sensor and generate a distance image on the basis of the acquired received light signal;
acquire a position of a leading end of a medical instrument inserted into the subject and determine a corresponding part of the subject which corresponds to the position of the leading end of the medical instrument in the subject;
acquire, as a leading end position image indicating the position of the leading end of the medical instrument in the subject, a transmission image of the corresponding part of the subject;
detect unevenness of a surface shape of the corresponding part of the subject on the basis of the generated distance image; and
transform the transmission image of the corresponding part of the subject to a shape fitted to the detected unevenness of the surface shape of the corresponding part of the subject to generate a projection image fitted to the surface shape of the corresponding part of the subject; and
a projector including a display optical element that displays the generated projection image, a projection light source that emits projection light so as to be incident on the display optical element, and a projection lens that projects the projection image emitted from the display optical element to the surface of the corresponding part of the subject.

2. The projection mapping apparatus according to claim 1, wherein the processor is further configured to acquire the position of the leading end of the medical instrument in the subject on the basis of the transmission image of the subject and a known internal structure of the subject.

3. The projection mapping apparatus according to claim 1, wherein:
the medical instrument is inserted along a known path in the subject; and
the processor is further configured to:
acquire an amount of insertion of the medical instrument into the subject;
compare the amount of insertion with the known path; and
acquire the position of the leading end of the medical instrument in the subject on the basis of a result of the comparing.

4. The projection mapping apparatus according to claim 1, wherein:
an acceleration sensor and a gyro sensor are provided at the leading end of the medical instrument; and
the processor is further configured to:
detect a moving direction and an amount of movement of the leading end of the medical instrument from an insertion position where the medical instrument is inserted into the subject, on the basis of outputs from the acceleration sensor and the gyro sensor; and
acquire the position of the leading end of the medical instrument in the subject on the basis of detection results of the moving direction and the amount of movement.

5. The projection mapping apparatus according to claim 1, wherein:

an imager is provided at the leading end of the medical instrument; and the processor is further configured to:

acquire insertion path information indicating an insertion path of the leading end of the medical instrument in the subject on the basis of an image captured by the imager; and acquire the position of the leading end of the medical instrument in the subject on the basis of an insertion position where the medical instrument is inserted into the subject and the acquired insertion path information.

6. The projection mapping apparatus according to claim 1, wherein the processor is further configured to:

switch wavelengths of the measurement light emitted from the light source to the subject before the distance image is generated;

control the light source such that the light source emits the measurement light of one of the wavelengths at which intensity of the measurement light incident on the light receiving elements is the highest among the wavelengths of the measurement light; and generate the distance image in a case in which the light source irradiates the subject with the measurement light of the one of the wavelengths at which the intensity of the measurement light incident on the light receiving elements is the highest.

7. The projection mapping apparatus according to claim 6, wherein:

the light source includes a plurality of light source units that emit the measurement light of wavelengths different from each other, to irradiate the subject with the measurement light of the different wavelengths; and the processor is further configured to:

switch the light source units that emit the measurement light; and perform control such that one of the light source units that emits the measurement light of the one of the wavelengths at which the intensity of the measurement light incident on the light receiving elements is the highest irradiates the subject with the measurement light.

8. The projection mapping apparatus according to claim 1, wherein the processor is further configured to:

acquire a projection range of the projection image projected to the surface of the subject, on the basis of a focal length of the projection lens, a distance to the surface of the subject which is indicated by the generated distance image, and the generated projection image; and set a generation range in which the distance image is generated in correspondence with the acquired projection range.

9. The projection mapping apparatus according to claim 1, wherein the distance image is generated by the processor by further configuring the processor to:

acquire, from the acquired received light signal, an indication of distance information corresponding to a time of flight of the measurement light that is emitted from the light source to irradiate the subject, then reflected by the subject and received by the each light receiving element of the plurality of light receiving elements; and generate the distance image on the basis of the distance information.

10. The projection mapping apparatus according to claim 1, wherein the processor is further configured to:

recognize the unevenness of the surface shape of the corresponding part of the subject on the basis of the surface shape of the subject detected from the generated distance image and the acquired position of the leading end of the medical instrument in the subject; and transform the leading end position image to a shape fitted to the recognized unevenness of the surface shape of the corresponding part of the subject to generate the projection image.

11. The projection mapping apparatus according to claim 1, wherein:

the processor is further configured to decide a display position and a size of the projection image displayed on the display optical element as a display position and a size of the projection image projected so as to overlap the corresponding part of the subject, on the basis of a distance from the projector to the surface of the corresponding part of the subject which is determined by the generated distance image and the acquired position of the leading end of the medical instrument in the subject, and focal length information of the projection lens, and the display optical element displays the projection image at the display position and in the size decided by the processor.

* * * * *